United States Patent
Malecki et al.

(10) Patent No.: US 8,066,701 B2
(45) Date of Patent: *Nov. 29, 2011

(54) ENERGY BASED DEVICES AND METHODS FOR TREATMENT OF PATENT FORAMEN OVALE

(75) Inventors: William Malecki, San Francisco, CA (US); Dan Francis, Mountain View, CA (US); Kenneth Horne, Palo Alto, CA (US); Mark E. Deem, Mountain View, CA (US); Hanson S. Gifford, III, Woodside, CA (US); Jose Alejandro, Sunnyvale, CA (US)

(73) Assignee: Terumo Kabushiki Kaisha, Tokyo (JP)

( * ) Notice: Subject to any disclaimer, the term of this patent is extended or adjusted under 35 U.S.C. 154(b) by 1494 days.

This patent is subject to a terminal disclaimer.

(21) Appl. No.: 11/472,923

(22) Filed: Jun. 21, 2006

(65) Prior Publication Data

US 2006/0241582 A1   Oct. 26, 2006

Related U.S. Application Data

(60) Continuation of application No. 11/249,566, filed on Oct. 12, 2005, which is a continuation of application No. 10/958,533, filed on Oct. 4, 2004, which is a division of application No. 10/679,245, filed on Oct. 2, 2003, now Pat. No. 6,939,348.

(60) Provisional application No. 60/458,854, filed on Mar. 27, 2003, provisional application No. 60/478,035, filed on Jun. 11, 2003, provisional application No. 60/490,082, filed on Jul. 24, 2003.

(51) Int. Cl.
*A61B 18/14* (2006.01)
(52) U.S. Cl. .............. 606/41; 606/27; 606/213
(58) Field of Classification Search ............ 606/27–31, 606/41, 47–50, 213–215; 607/101, 102, 607/122; 128/898
See application file for complete search history.

(56) References Cited

U.S. PATENT DOCUMENTS 2,275,167 A    3/1942  Bierman
(Continued)

FOREIGN PATENT DOCUMENTS

EP    135840 A2    4/1985
(Continued)

OTHER PUBLICATIONS

Besio et al., "Quantizing the Depth of Bioelectrical Sources for Non-Invasive 3D Imaging," *IJBEM*, vol. 7, No. 2, (2005), 4 pages total.

(Continued)

*Primary Examiner* — Michael Peffley
(74) *Attorney, Agent, or Firm* — Oblon, Spivak, McClelland, Maier & Neustadt, L.L.P.

(57) ABSTRACT

Methods and apparatus for treatment of patent foramen ovale (PFO) provide for applying energy to tissues adjacent the PFO with a catheter device to substantially close the PFO acutely. Apparatus generally includes a catheter device having at least one energy transmission member at or near its distal end configured to apply energy to PFO tissues to acutely, substantially close the PFO. Applied energy may be monopolar or bipolar radiofrequency energy or any other suitable energy, such as laser, microwave, ultrasound, resistive heating or the like. Some embodiments of a catheter device further include one or more tissue apposition members near the distal end for helping bring PFO tissues together, such as a PFO covering member, a vacuum applying member and/or the like. PFO closure via energy-based approaches of the invention may help prevent stroke, treat migraine headache, and possibly treat or prevent other medical conditions.

14 Claims, 14 Drawing Sheets

U.S. PATENT DOCUMENTS

| | | | |
|---|---|---|---|
| 2,580,628 A | 1/1952 | Welsh | |
| 2,888,928 A | 6/1959 | Seiger | |
| 3,490,442 A | 1/1970 | Streu | |
| 3,862,627 A | 1/1975 | Hans, Sr. | |
| 3,874,388 A | 4/1975 | King et al. | |
| 3,906,955 A | 9/1975 | Roberts | |
| 4,307,720 A | 12/1981 | Weber, Jr. | |
| 4,326,529 A | 4/1982 | Doss et al. | |
| 4,473,077 A | 9/1984 | Noiles et al. | |
| 4,485,817 A | 12/1984 | Swiggett | |
| 4,532,924 A | 8/1985 | Auth et al. | |
| 4,556,065 A | 12/1985 | Hoffmann | |
| 4,562,838 A | 1/1986 | Walker | |
| 4,590,934 A | 5/1986 | Malis et al. | |
| 4,682,596 A | 7/1987 | Bales et al. | |
| 4,788,975 A | 12/1988 | Shturman et al. | |
| 4,798,594 A | 1/1989 | Hillstead | |
| 4,832,048 A | 5/1989 | Cohen | |
| 4,884,567 A | 12/1989 | Elliott et al. | |
| 4,895,565 A | 1/1990 | Hillstead | |
| 4,911,159 A | 3/1990 | Johnson et al. | |
| 4,919,129 A | 4/1990 | Weber, Jr. et al. | |
| 4,929,246 A | 5/1990 | Sinofsky | |
| 4,976,711 A | 12/1990 | Parins et al. | |
| 4,986,889 A | 1/1991 | Charamathieu et al. | |
| 5,041,095 A | 8/1991 | Littrell | |
| 5,042,707 A | 8/1991 | Taheri | |
| 5,055,100 A | 10/1991 | Olsen | |
| 5,056,517 A | 10/1991 | Fenici | |
| 5,057,107 A | 10/1991 | Parins et al. | |
| 5,071,417 A | 12/1991 | Sinofsky | |
| 5,071,418 A | 12/1991 | Rosenbaum | |
| 5,078,717 A | 1/1992 | Parins et al. | |
| 5,099,827 A | 3/1992 | Melzer et al. | |
| RE33,925 E | 5/1992 | Bales et al. | |
| 5,125,928 A | 6/1992 | Parins et al. | |
| 5,156,608 A | 10/1992 | Troidl et al. | |
| 5,156,613 A | 10/1992 | Sawyer | |
| 5,171,311 A | 12/1992 | Rydell | |
| 5,195,959 A | 3/1993 | Smith | |
| 5,196,007 A | 3/1993 | Ellman et al. | |
| 5,197,963 A | 3/1993 | Parins | |
| 5,207,670 A | 5/1993 | Sinofsky | |
| 5,209,756 A | 5/1993 | Seedhom et al. | |
| 5,290,278 A | 3/1994 | Anderson | |
| 5,292,362 A | 3/1994 | Bass et al. | |
| 5,295,955 A | 3/1994 | Rosen et al. | |
| 5,300,065 A | 4/1994 | Anderson | |
| 5,336,221 A | 8/1994 | Anderson | |
| 5,336,252 A | 8/1994 | Cohen | |
| 5,342,413 A | 8/1994 | Hirschberg et al. | |
| 5,345,935 A | 9/1994 | Hirsch et al. | |
| 5,370,675 A | 12/1994 | Edwards et al. | |
| 5,380,304 A | 1/1995 | Parker | |
| 5,383,917 A | 1/1995 | Desai et al. | |
| 5,405,322 A | 4/1995 | Lennox et al. | |
| 5,409,479 A | 4/1995 | Dew et al. | |
| 5,409,481 A | 4/1995 | Poppas et al. | |
| 5,500,012 A | 3/1996 | Brucker et al. | |
| 5,505,730 A | 4/1996 | Edwards | |
| 5,507,744 A * | 4/1996 | Tay et al. | 606/50 |
| 5,540,677 A | 7/1996 | Sinofsky | |
| 5,569,239 A | 10/1996 | Sinofsky | |
| 5,571,216 A | 11/1996 | Anderson | |
| 5,575,772 A | 11/1996 | Lennox | |
| 5,584,872 A | 12/1996 | Lafontaine et al. | |
| 5,611,794 A | 3/1997 | Sauer et al. | |
| 5,620,481 A | 4/1997 | Desai et al. | |
| 5,626,607 A | 5/1997 | Malecki et al. | |
| 5,662,643 A | 9/1997 | Kung et al. | |
| 5,665,109 A | 9/1997 | Yoon | |
| 5,669,934 A | 9/1997 | Sawyer | |
| 5,693,078 A | 12/1997 | Desai et al. | |
| 5,709,224 A | 1/1998 | Behl | |
| 5,713,891 A | 2/1998 | Poppas | |
| 5,725,522 A | 3/1998 | Sinofsky | |
| 5,730,742 A | 3/1998 | Wojciechowicz | |
| 5,749,895 A | 5/1998 | Sawyer et al. | |
| 5,782,899 A | 7/1998 | Imran | |
| 5,814,065 A | 9/1998 | Diaz | |
| 5,824,015 A | 10/1998 | Sawyer | |
| 5,827,265 A | 10/1998 | Glinsky et al. | |
| 5,846,196 A | 12/1998 | Siekmeyer et al. | |
| 5,855,312 A | 1/1999 | Toledano | |
| 5,871,443 A | 2/1999 | Edwards et al. | |
| 5,919,200 A | 7/1999 | Stambaugh et al. | |
| 5,925,078 A | 7/1999 | Anderson | |
| 5,928,266 A | 7/1999 | Kontos | |
| 5,931,165 A | 8/1999 | Reich et al. | |
| 5,944,738 A | 8/1999 | Amplatz et al. | |
| 5,972,023 A | 10/1999 | Tanner et al. | |
| 5,972,024 A | 10/1999 | Northrup, III et al. | |
| 6,004,316 A | 12/1999 | Laufer | |
| 6,012,457 A | 1/2000 | Lesh | |
| 6,036,699 A | 3/2000 | Andreas et al. | |
| 6,050,994 A | 4/2000 | Sherman | |
| 6,056,760 A | 5/2000 | Koike et al. | |
| 6,063,081 A | 5/2000 | Mulier | |
| 6,063,085 A | 5/2000 | Tay | |
| 6,083,223 A | 7/2000 | Baker | |
| 6,086,570 A | 7/2000 | Aboul-Hosn et al. | |
| 6,086,586 A | 7/2000 | Hooven | |
| 6,087,552 A | 7/2000 | Gregory | |
| 6,092,528 A | 7/2000 | Edwards | |
| 6,132,429 A | 10/2000 | Baker | |
| 6,149,660 A | 11/2000 | Laufer et al. | |
| 6,156,032 A | 12/2000 | Lennox | |
| 6,168,594 B1 | 1/2001 | Lafontaine | |
| 6,211,335 B1 | 4/2001 | Owen et al. | |
| 6,221,068 B1 | 4/2001 | Fried et al. | |
| 6,236,875 B1 | 5/2001 | Bucholz | |
| 6,248,124 B1 | 6/2001 | Pedros et al. | |
| 6,257,241 B1 | 7/2001 | Wampler | |
| 6,290,674 B1 | 9/2001 | Roue et al. | |
| 6,302,898 B1 | 10/2001 | Edwards et al. | |
| 6,323,037 B1 | 11/2001 | Lauto et al. | |
| 6,325,798 B1 | 12/2001 | Edwards et al. | |
| 6,355,030 B1 | 3/2002 | Aldrich et al. | |
| 6,358,246 B1 | 3/2002 | Behl et al. | |
| 6,375,668 B1 | 4/2002 | Gifford et al. | |
| 6,383,198 B1 | 5/2002 | Hamilton | |
| 6,391,048 B1 | 5/2002 | Ginn et al. | |
| 6,391,049 B1 | 5/2002 | McNally et al. | |
| 6,398,779 B1 | 6/2002 | Buysse et al. | |
| 6,398,782 B1 | 6/2002 | Pecor et al. | |
| 6,398,797 B2 | 6/2002 | Bombard et al. | |
| 6,401,720 B1 | 6/2002 | Stevens et al. | |
| 6,409,720 B1 | 6/2002 | Hissong et al. | |
| 6,413,254 B1 | 7/2002 | Hissong et al. | |
| 6,419,669 B1 | 7/2002 | Frazier et al. | |
| 6,423,057 B1 | 7/2002 | He et al. | |
| 6,436,088 B2 | 8/2002 | Frazier et al. | |
| 6,451,013 B1 | 9/2002 | Bays et al. | |
| 6,456,865 B2 | 9/2002 | Samson | |
| 6,458,100 B2 | 10/2002 | Roue et al. | |
| 6,475,213 B1 | 11/2002 | Whayne et al. | |
| 6,482,224 B1 | 11/2002 | Michler et al. | |
| 6,514,250 B1 | 2/2003 | Jahns et al. | |
| 6,558,314 B1 | 5/2003 | Adelman et al. | |
| 6,558,382 B2 | 5/2003 | Jahns et al. | |
| 6,562,037 B2 | 5/2003 | Paton et al. | |
| 6,583,117 B2 | 6/2003 | Owen et al. | |
| 6,584,360 B2 | 6/2003 | Francischelli et al. | |
| 6,589,237 B2 | 7/2003 | Woloszko | |
| 6,606,523 B1 | 8/2003 | Jenkins | |
| 6,641,604 B1 | 11/2003 | Adelman | |
| 6,645,202 B1 | 11/2003 | Pless et al. | |
| 6,645,225 B1 | 11/2003 | Atkinson | |
| 6,648,897 B2 | 11/2003 | Hamilton | |
| 6,652,518 B2 | 11/2003 | Wellman et al. | |
| 6,669,693 B2 | 12/2003 | Friedman | |
| 6,676,685 B2 | 1/2004 | Pedros et al. | |
| 6,682,546 B2 | 1/2004 | Amplatz | |
| 6,692,450 B1 | 2/2004 | Coleman | |
| 6,702,835 B2 | 3/2004 | Ginn | |
| 6,712,804 B2 | 3/2004 | Roue et al. | |
| 6,712,836 B1 | 3/2004 | Berg et al. | |

| | | |
|---|---|---|
| 6,716,211 B2 | 4/2004 | Mulier et al. |
| 6,726,718 B1 | 4/2004 | Carlyle et al. |
| 6,730,108 B2 | 5/2004 | Van Tassel et al. |
| 6,733,498 B2 | 5/2004 | Paton et al. |
| 6,736,810 B2 | 5/2004 | Hoey et al. |
| 6,755,790 B2 | 6/2004 | Stewart et al. |
| 6,770,072 B1 | 8/2004 | Truckai et al. |
| 6,776,784 B2 | 8/2004 | Ginn |
| 6,790,218 B2 | 9/2004 | Jayaraman |
| 6,846,319 B2 | 1/2005 | Ginn et al. |
| 6,887,238 B2 | 5/2005 | Jahns |
| 6,893,431 B2 | 5/2005 | Naimark et al. |
| 6,893,442 B2 | 5/2005 | Whayne |
| 6,918,908 B2 | 7/2005 | Bonner et al. |
| 6,926,716 B2 | 8/2005 | Baker et al. |
| 6,929,644 B2 | 8/2005 | Truckai et al. |
| 6,932,812 B2 | 8/2005 | Crowley et al. |
| 6,939,348 B2 | 9/2005 | Malecki et al. |
| 6,946,134 B1 | 9/2005 | Rosen et al. |
| 6,960,205 B2 | 11/2005 | Jahns et al. |
| 7,025,756 B2 | 4/2006 | Frazier et al. |
| 7,094,215 B2 | 8/2006 | Davison et al. |
| 7,165,552 B2 | 1/2007 | Deem et al. |
| 7,186,251 B2 | 3/2007 | Malecki et al. |
| 7,238,182 B2 | 7/2007 | Swoyer et al. |
| 7,293,562 B2 | 11/2007 | Malecki et al. |
| 7,311,701 B2 | 12/2007 | Deem et al. |
| 2001/0020166 A1 | 9/2001 | Daly et al. |
| 2001/0037129 A1 | 11/2001 | Thill |
| 2001/0051803 A1 | 12/2001 | Desai et al. |
| 2002/0128672 A1 | 9/2002 | Dinger et al. |
| 2002/0143322 A1 | 10/2002 | Haghighi |
| 2002/0156472 A1 | 10/2002 | Lee et al. |
| 2003/0028189 A1 | 2/2003 | Woloszko et al. |
| 2003/0045893 A1 | 3/2003 | Ginn |
| 2003/0045901 A1 | 3/2003 | Opolski |
| 2003/0050665 A1 | 3/2003 | Ginn |
| 2003/0065364 A1 | 4/2003 | Wellman et al. |
| 2003/0069570 A1 | 4/2003 | Witzel |
| 2003/0078578 A1 | 4/2003 | Truckai et al. |
| 2003/0092988 A1 | 5/2003 | Makin |
| 2003/0093071 A1 | 5/2003 | Hauck et al. |
| 2003/0120268 A1 | 6/2003 | Bertolero et al. |
| 2003/0144652 A1 | 7/2003 | Baker et al. |
| 2003/0144694 A1 | 7/2003 | Chanduszko et al. |
| 2003/0158551 A1 | 8/2003 | Paton et al. |
| 2003/0199868 A1 | 10/2003 | Desai et al. |
| 2003/0208232 A1 | 11/2003 | Blaeser |
| 2003/0225421 A1 | 12/2003 | Peavey et al. |
| 2003/0233091 A1 | 12/2003 | Whayne et al. |
| 2004/0059347 A1 | 3/2004 | Hamilton |
| 2004/0092973 A1 | 5/2004 | Chanduszko et al. |
| 2004/0098031 A1 | 5/2004 | Van der Burg et al. |
| 2004/0098042 A1 | 5/2004 | Devellian et al. |
| 2004/0102721 A1 | 5/2004 | Mckinley |
| 2004/0143292 A1 | 7/2004 | Marino et al. |
| 2004/0153057 A1 | 8/2004 | Davison |
| 2004/0153098 A1 | 8/2004 | Chin et al. |
| 2004/0176799 A1 | 9/2004 | Chanduszko et al. |
| 2004/0220596 A1 | 11/2004 | Frazier et al. |
| 2004/0243122 A1* | 12/2004 | Auth et al. ............... 606/41 |
| 2004/0249398 A1 | 12/2004 | Ginn |
| 2005/0021016 A1 | 1/2005 | Malecki et al. |
| 2005/0021059 A1 | 1/2005 | Cole et al. |
| 2005/0033288 A1 | 2/2005 | Auth et al. |
| 2005/0033327 A1 | 2/2005 | Gainor et al. |
| 2005/0034735 A1 | 2/2005 | Deem et al. |
| 2005/0055050 A1 | 3/2005 | Alfaro |
| 2005/0065506 A1 | 3/2005 | Phan |
| 2005/0065509 A1 | 3/2005 | Coldwell et al. |
| 2005/0070923 A1 | 3/2005 | McIntosh |
| 2005/0075665 A1 | 4/2005 | Brenzel et al. |
| 2005/0119675 A1 | 6/2005 | Adams et al. |
| 2005/0125032 A1 | 6/2005 | Whisenant et al. |
| 2005/0171526 A1 | 8/2005 | Rioux et al. |
| 2005/0187568 A1 | 8/2005 | Klenk et al. |
| 2005/0192626 A1 | 9/2005 | Widomski et al. |
| 2005/0192627 A1 | 9/2005 | Whisenant et al. |
| 2005/0192654 A1 | 9/2005 | Chanduszko et al. |
| 2005/0209636 A1 | 9/2005 | Widomski et al. |
| 2005/0216054 A1 | 9/2005 | Widomski et al. |
| 2005/0251201 A1 | 11/2005 | Roue et al. |
| 2005/0256532 A1 | 11/2005 | Nayak et al. |
| 2005/0267495 A1 | 12/2005 | Ginn et al. |
| 2005/0267525 A1 | 12/2005 | Chanduszko |
| 2006/0009762 A1 | 1/2006 | Whayne |
| 2006/0027241 A1 | 2/2006 | Malecki et al. |
| 2006/0036284 A1 | 2/2006 | Blaeser et al. |
| 2006/0052821 A1 | 3/2006 | Abbott et al. |
| 2006/0069408 A1 | 3/2006 | Kato |
| 2006/0079870 A1 | 4/2006 | Barry |
| 2006/0079887 A1 | 4/2006 | Buysse et al. |
| 2006/0173510 A1 | 8/2006 | Besio et al. |
| 2006/0241581 A1 | 10/2006 | Malecki et al. |
| 2006/0241582 A1 | 10/2006 | Malecki et al. |
| 2006/0241583 A1 | 10/2006 | Malecki et al. |
| 2006/0241584 A1 | 10/2006 | Malecki et al. |
| 2006/0247612 A1 | 11/2006 | Malecki et al. |
| 2006/0276779 A1 | 12/2006 | Malecki et al. |
| 2007/0010806 A1 | 1/2007 | Malecki et al. |
| 2007/0078485 A1 | 4/2007 | Deem et al. |
| 2007/0088355 A9 | 4/2007 | Auth et al. |
| 2007/0123851 A1 | 5/2007 | Alejandro et al. |
| 2007/0123852 A1 | 5/2007 | Deem et al. |
| 2007/0299434 A1 | 12/2007 | Malecki et al. |
| 2008/0004658 A1 | 1/2008 | Malecki et al. |
| 2008/0140113 A1 | 6/2008 | Taimisto et al. |

FOREIGN PATENT DOCUMENTS

| | | |
|---|---|---|
| EP | 199694 A2 | 10/1986 |
| EP | 0265532 A1 | 5/1988 |
| EP | 0375556 A1 | 6/1990 |
| EP | 0428812 A1 | 5/1991 |
| EP | 0947165 A1 | 10/1999 |
| GB | 1260919 | 1/1972 |
| GB | 1550676 | 8/1979 |
| GB | 2 359 024 A | 8/2001 |
| WO | 85/00018 A1 | 1/1985 |
| WO | 87/04081 A1 | 7/1987 |
| WO | 90/04352 A1 | 5/1990 |
| WO | 91/15996 A1 | 10/1991 |
| WO | 92/04864 A1 | 4/1992 |
| WO | 93/05705 A1 | 4/1993 |
| WO | 93/15791 A1 | 8/1993 |
| WO | 94/00178 A1 | 1/1994 |
| WO | 98/07375 A1 | 2/1998 |
| WO | 99/18862 A1 | 4/1999 |
| WO | 99/18864 A1 | 4/1999 |
| WO | 99/18870 A1 | 4/1999 |
| WO | 99/18871 A1 | 4/1999 |
| WO | 99/23959 A1 | 5/1999 |
| WO | 99/49788 A | 10/1999 |
| WO | 00/07506 A2 | 2/2000 |
| WO | 00/09027 A1 | 2/2000 |
| WO | 01/13810 A1 | 3/2001 |
| WO | 01/78596 A1 | 10/2001 |
| WO | 01/82778 A | 11/2001 |
| WO | 03/022159 A1 | 3/2003 |
| WO | 03/022160 A1 | 3/2003 |
| WO | 03/026496 A2 | 4/2003 |
| WO | 03/053493 A2 | 7/2003 |
| WO | 03/071957 A2 | 9/2003 |
| WO | 03/082076 A2 | 10/2003 |
| WO | 03/094742 A1 | 11/2003 |
| WO | 2004/019791 A2 | 3/2004 |
| WO | 2004/043266 A2 | 5/2004 |
| WO | 2004/069055 A2 | 8/2004 |
| WO | 2004/082532 A1 | 9/2004 |
| WO | 2004/091411 A2 | 10/2004 |
| WO | 2005/006990 A2 | 1/2005 |
| WO | 2005/027753 A1 | 3/2005 |
| WO | 2005/034738 A2 | 4/2005 |
| WO | 2005/074814 A2 | 8/2005 |
| WO | 2005/046487 A1 | 12/2005 |
| WO | 2005/115256 A | 12/2005 |

OTHER PUBLICATIONS

Anzola et al., "Potential Source of Cerebral Embolism in Migraine with Aura," *Neurology* (1999) 52(39): 1622.

Athiraman et al., "Selective Phothermal Tissue Interaction Using 805-nm Laser and Indocyanine Green in Tissue Welding," *Journal of X-Ray Science and Technolgy*, vol. 12, No. 2 (2004), pp. 117-126.

Cordis Corporation, Cordis Cucor® Lumeleo™ Electorode Catheters [brochure], Cordis Corporation, (Dec. 1984), 2 pages.

De Castro et al., "Morphological and Functional Characteristics of patent Foramen Ovale and Their Embolic Implications," *Stroke* (Oct. 2002), pp. 2407-2413.

Del Sette, "Migraine with Aura and Right-to-Left Shunt on Transcranial Doppler: A Case Control Study," *Cerebrovas Dis* (1998) 8:327-330.

Fenner et al., "Shear Strength of Tissue Bonds as a Fuction of Bonding Temperature: A Proposed Mechanism for Laser-Assisted Tissue Welding," *Lasers in Medical Science*, vol. 7, (1992), pp. 39-43.

Gillette, "Catheter Ablation in Dysrhythmias," *Cardio*, (Mar. 1984), pp. 67-69.

Godlewski et al., "Applications and Mechanisms of Laser Tissue Welding in 1995: Reivew," *Proc. SPIE*, vol. 2623, (Jan. 1996), pp. 334-341.

Ho et al., "Morphological Features Pertinent to Interventional Closure of Patent Oval Foramen," *J Interventional Cardiology*, vol. 16 No. 1, (2003), pp. 33-34.

Kennedy et al., "High-burst-Strength, feedback-controlled bipolar vessel sealing," *Surg Endosc* (1998) 12:876-878.

Koenig et al., "Role of Intracardiac Echocardiographic Guidance in Transcatheter Closure of Atiral Septal Defects and Patent Foramen Ovale Using the Amplatzer® Device," *J. Interventional Cardiology*, (2003) 16 (1): 51-62.

Morady, "Transvenous Catheter Ablation of a Posterospetial Accessory Pathway in a Patient with the Wolff Parkinson-White Syndrome," *The New England Journal of Medicine*, (Mar. 15, 1984), 310(11): 705-707.

Morandi et al., "Transcatheter Closure of Patent Foramen Ovale: A New Migraine Treatment?" *J Interventional Cardiology*, (2003), 16(1): 39-42.

Olson et al., "Developing An Animal Model for the Study of Fusion Using RF Energy," *Proc. SPIE*, vol. 5312, (2004), pp. 147-161.

Ott et al., "Comparative in Vitro Study of Tissue Welding Using a 808 nm Diode Laser and a Ho:YAG laser," *Lasers Med Sci*, vol. 16, (2001) pp. 260-266.

Pfleger, "Haemodynamic Quantification of Different Provocation Manoeuvres by Siumultaneous Measurement of Right and Left Atrial Pressure: Implications for the Echocardiographic Detection of Persistent Foramen Ovale," *Eur J Echocardiography* (2001) 2: 88-93.

Polgar et al., "A New Technique for closed-Chest Human His Bundle Ablation Using Suction Electrode Catheter and DC Shock," In: Perez Gomez F, ed. Cardiac Pacing Electrophysiology Tachyarrhythmias. Madrid, Spain: Grouz Publishers; 1985:1582-1586.

Polgar et al., "Comparison of Two Different Techniques for Closed-Chest His Bundle *Ablation*," *In: Perez Gomez F, ed*. Cardiac pacing Electrophysiology Tachyarrhythmias. Madrid, Spain: Grouz Publishers; 1985:1578-1587.

Polgar, "Closed Chested Ablation of His Bundle: A New Technique Using Suction Electorde Catheter and DC Shock," *Nachdruck Aus: Cardio Pacing*, (1983), pp. 883-890.

Poppas et al., "Temperature-Controlled Laser Photocoagulation of Soft Tissue: in Vivo Evaluation Using a Tissue Welding Model," *Lasers Surg Med.*, vol. 18, No. 4, (1996), pp. 335-344.

Stewart et al., "Laser Assisted Vascular Welding with Real Time Temperature Control," *Lasers Surg Med.*, vol. 19, No. 1, (1996), pp. 9-16.

Stuart, "What's All the Flap About PFO Closure?," *Start-Up: Windhover's Review of Emerging Medical Ventures*, (Nov. 10, 2004), pp. 9-14.

Sztajzel et al., "Patent Foramen Ovale, a Possible Cause of Symptomatic Migraine: A Study of 74 Patients with Acute Ischemic Stroke," *Cerebrovas Dis* (2002) 13: 102-106.

Tang et al, "Morphologic Changes in Collagen Fibers after 830 nm Diode Laser Welding," *Lasers Surg Med.*, vol. 21, No. 5 (1997), pp. 438-443.

Tang et al., "Quantitative Changes in Collagen Levels Following 830-nm Diode Laser Welding," *Lasers Surg Med.*, vol. 22, No. 4, (1998), pp. 207-211.

Thomas, "Patent Foramen Ovale with Right-to-left Shunting: Echocariographic Alternatives," *Eur J Echocariography* (2001) 2:74-75.

Wilmhurst et al., "Effect on Migraine of Closure of Cardiac Right-to-Left Shunts to Prevent Recurrence of Decompression Illness of Illness or Stroke or for Haemodynamic Reasons," *The Lancet*, vol. 356, (Nov. 11, 2000), pp. 1648-1651.

Wilmhurst et al., "Relationship between Migraine and Cardiac and Pulmonary Right to Left Shunts," *Clinical Science* (2001) 100:215-220.

European Search Report issued Nov. 24, 2010, in Patent Application No. 04758520.3.

U.S. Appl. No. 95,000,260, filed Jun. 22, 2007, Malecki et al.

U.S. Appl. No. 95/000,264, filed Jun. 18, 2007, Malecki et al.

Canadian Office Action issued on Mar. 8, 2011 in corresponding Canadian Application No. 2,519,559.

European Office Action issued Mar. 11, 2011, in Patent Application No. 04 758 520.3.

\* cited by examiner

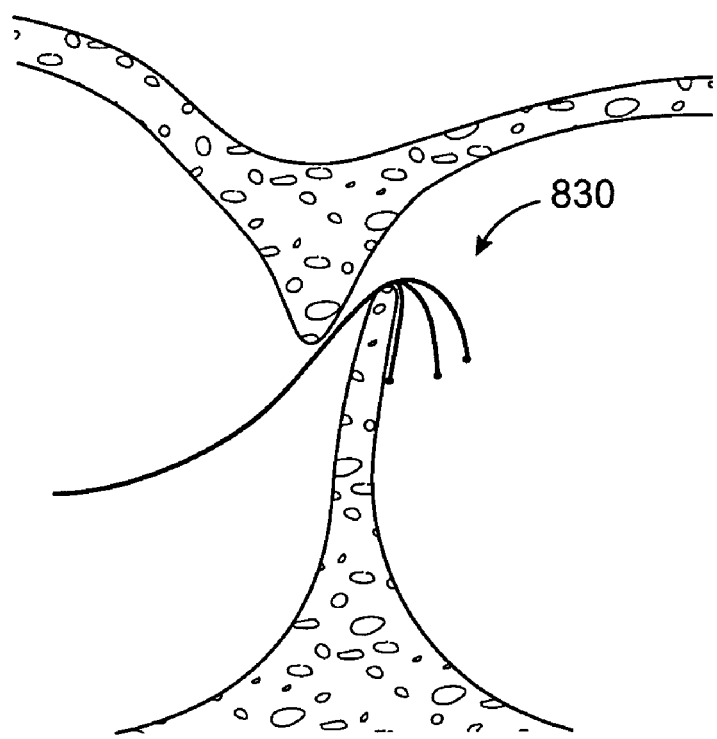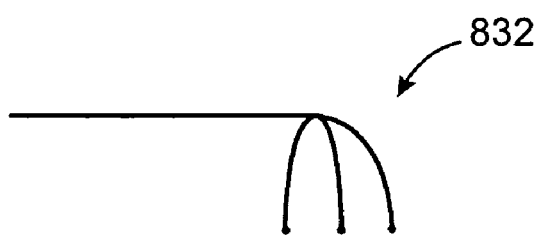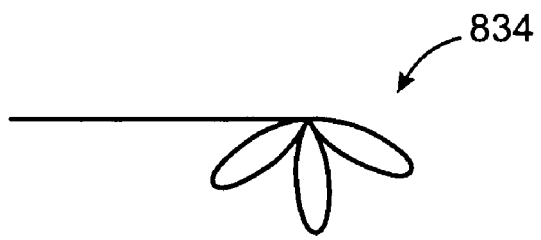
FIG. 10

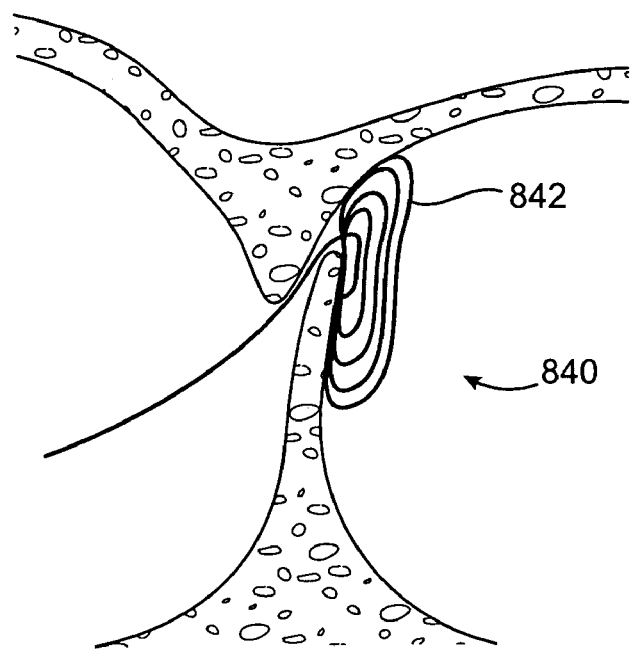
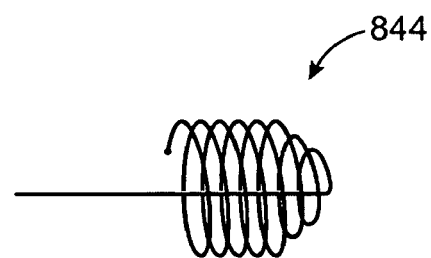
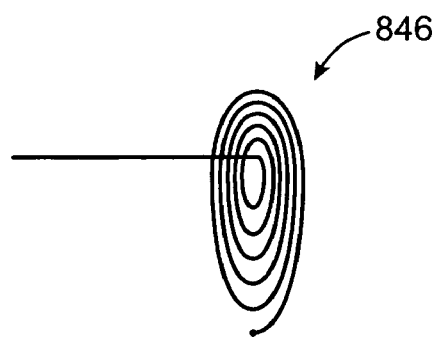
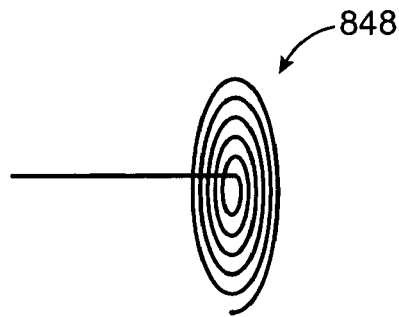
FIG. 11

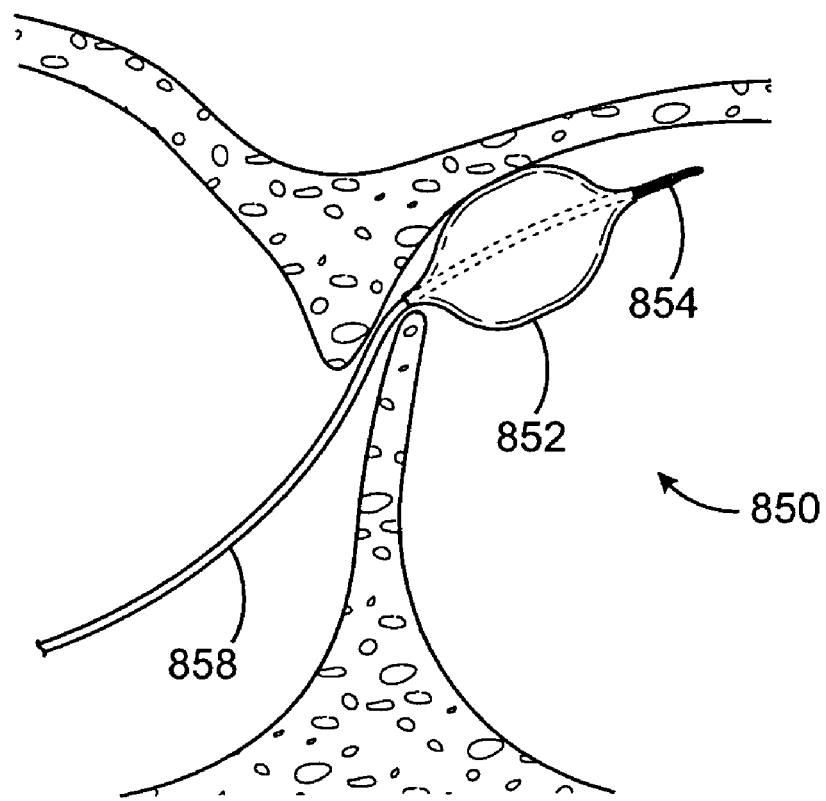
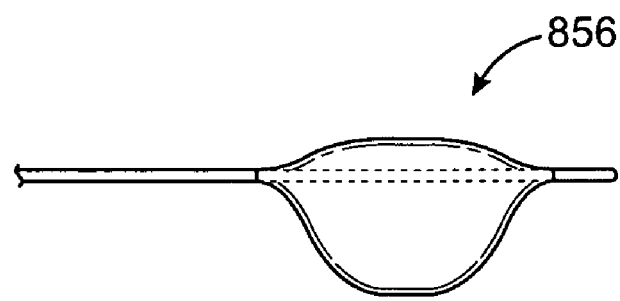
FIG. 12

ENERGY BASED DEVICES AND METHODS FOR TREATMENT OF PATENT FORAMEN OVALE

CROSS-REFERENCES TO RELATED APPLICATIONS

This application is a continuation of U.S. patent application Ser. No. 11/249,566, filed Oct. 12, 2005, which is a continuation of U.S. patent application Ser. No. 10/958,533, filed Oct. 4, 2004, which was a divisional of U.S. patent application Ser. No. 10/679,245, filed Oct. 2, 2003, now U.S. Pat. No. 6,939,348, which claimed priority to U.S. Provisional Patent Application Nos. 60/458,854, filed Mar. 27, 2003; 60/478,035, filed Jun. 11, 2003; and 60/490,082, filed Jul. 24, 2003, the full disclosures of which are incorporated herein by reference. This application is related to U.S. patent application Ser. No. 10/665,974, filed Sep. 18, 2003, now U.S. Pat. No. 7,165,552, the full disclosure of which is incorporated herein by reference.

BACKGROUND OF THE INVENTION

The invention generally relates to medical devices and methods. More specifically, the invention relates to energy based devices and methods for treatment of patent foramen ovale.

Fetal blood circulation is much different than adult circulation. Because fetal blood is oxygenated by the placenta, rather than the fetal lungs, blood is generally shunted away from the lungs to the peripheral tissues through a number of vessels and foramens that remain patent (i.e., open) during fetal life and typically close shortly after birth. For example, fetal blood passes directly from the right atrium through the foramen ovale into the left atrium, and a portion of blood circulating through the pulmonary artery trunk passes through the ductus arteriosus to the aorta. This fetal circulation is shown in attached FIG. 1.

At birth, as a newborn begins breathing, blood pressure in the left atrium rises above the pressure in the right atrium. In most newborns, a flap of tissue closes the foramen ovale and heals together. In approximately 20,000 babies born each year in the US, the flap of tissue is missing, and the hole remains open as an atrial septal defect (ASD). In a much more significant percentage of the population (estimates range from 5% to 20% of the entire population), the flap is present but does not heal together. This condition is known as a patent foramen ovale (PFO). Whenever the pressure in the right atrium rises above that in the left atrium, blood pressure can push this patent channel open, allowing blood to flow from the right atrium to the left atrium.

Patent foramen ovale has long been considered a relatively benign condition, since it typically has little effect on the body's circulation. More recently, however, it has been found that a significant number of strokes may be caused at least in part by PFO. In some cases, stroke may occur because a PFO allows blood containing small thrombi to flow directly from the venous circulation to the arterial circulation and into the brain, rather than flowing to the lungs where the thrombi can become trapped and gradually dissolved. In other cases, thrombi might form in the patent channel of the PFO itself and become dislodged when the pressures cause blood to flow from the right atrium to the left atrium. It has been estimated that patients with PFOs who have already had cryptogenic strokes have a 4% risk per year of having another stroke.

Further research is currently being conducted into the link between PFO and stroke. At the present time, if someone with a PFO has two or more strokes, the healthcare system in the U.S. may reimburse a surgical or other interventional procedure to definitively close the PFO. It is likely, however, that a more prophylactic approach would be warranted to close PFOs to prevent the prospective occurrence of a stroke. The cost and potential side-effects and complications of such a procedure must be low, however, since the event rate due to PFOs is relatively low. In younger patients, for example, PFOs sometimes close by themselves over time without any adverse health effects.

Another highly prevalent and debilitating condition—chronic migraine headache—has also been linked with PFO. Although the exact link has not yet been explained, PFO closure has been shown to eliminate or significantly reduce migraine headaches in many patients. Again, prophylactic PFO closure to treat chronic migraine headaches might be warranted if a relatively non-invasive procedure were available.

Currently available interventional therapies for PFO are generally fairly invasive and/or have potential drawbacks. One strategy is simply to close a PFO during open heart surgery for another purpose, such as heart valve surgery. This can typically be achieved via a simple procedure such as placing a stitch or two across the PFO with vascular suture. Performing open heart surgery purely to close an asymptomatic PFO or even a very small ASD, however, would be very hard to justify.

A number of interventional devices for closing PFOs percutaneously have also been proposed and developed. Most of these devices are the same as or similar to ASD closure devices. They are typically "clamshell" or "double umbrella" shaped devices which deploy an area of biocompatible metal mesh or fabric (ePTFE or Dacron, for example) on each side of the atrial septum, held together with a central axial element, to cover the PFO. This umbrella then heals into the atrial septum, with the healing response forming a uniform layer of tissue or "pannus" over the device. Such devices have been developed, for example, by companies such as Nitinol Medical Technologies, Inc. (Boston, Mass.) and AGA Medical, Inc. (White Bear Lake, Minn.). U.S. Pat. No. 6,401,720 describes a method and apparatus for thoracoscopic intracardiac procedures which may be used for treatment of PFO.

Although available devices may work well in some cases, they also face a number of challenges. Relatively frequent causes of complications include, for example, improper deployment, device embolization into the circulation and device breakage. In some instances, a deployed device does not heal into the septal wall completely, leaving an exposed tissue which may itself be a nidus for thrombus formation. Furthermore, currently available devices are generally complex and expensive to manufacture, making their use for prophylactic treatment of PFO impractical. Additionally, currently available devices typically close a PFO by placing material on either side of the tunnel of the PFO, compressing and opening the tunnel acutely, until blood clots on the devices and causes flow to stop.

Research into methods and compositions for tissue welding has been underway for many years. Of particular interest are technologies developed by McNally et. al., (as shown in U.S. Pat. No. 6,391,049) and Fusion Medical (as shown in U.S. Pat. Nos. 5,156,613, 5,669,934, 5,824,015 and 5,931,165). These technologies all disclose energy delivery to tissue solders and patches to join tissue and form anastamoses between arteries, bowel, nerves, etc. Also of interest are a number of patents by inventor Sinofsky, relating to laser suturing of biological materials (e.g., U.S. Pat. Nos. 5,725, 522, 5,569,239, 5,540,677 and 5,071,417). None of these disclosures, however, show methods or apparatus suitable for positioning the tissues of the PFO for welding or for delivering the energy to a PFO to be welded.

Causing thermal trauma to a patent ovale has been described in two patent applications by Stambaugh et al. (PCT Publication Nos. WO 99/18870 and WO 99/18871). The devices and methods described, however, cause trauma to PFO tissues to hopefully eventually cause scar tissue formation which will close the PFO. Using such devices and methods, the PFO actually remains patent immediately after the procedure and only closes sometime later. Therefore, a physician may not know whether the treatment has worked until long after the treatment procedure has been performed. Frequently, scar tissue may fail to form or may form incompletely, resulting in a still patent PFO.

Therefore, it would be advantageous to have improved methods and apparatus for treating a PFO. Ideally, such methods and apparatus would help seal the PFO during, immediately after or soon after performing a treatment procedure. Also ideally, such devices and methods would leave no foreign material (or very little material) in a patient's heart. Furthermore, such methods and apparatus would preferably be relatively simple to manufacture and use, thus rendering prophylactic treatment of PFO, such as for stroke prevention, a viable option. At least some of these objectives will be met by the present invention.

BRIEF SUMMARY OF THE INVENTION

The present invention generally provides devices and methods for treating patent foramen ovale (PFO). More specifically, the devices and methods involve advancing a catheter device to a position in the heart for treating the patent foramen ovale and applying energy to (or removing energy from) tissues adjacent a PFO to substantially close the PFO acutely. By "substantially," it is meant that a stable tissue bridge will be formed across the PFO, which will withstand physiologic pressures. A substantially closed PFO, however, may still have one or more small gaps or openings, which will in at least some cases close over time via the healing process. By "acutely," it is meant that the PFO is substantially closed when the closure procedure is completed. Thus, acute closure distinguishes devices and methods of the present invention from prior protocols, which rely on delayed PFO closure via tissue healing and scarring. "Acutely," for purposes of this application, does not mean temporarily, since devices and methods of the present invention will typically provide for permanent (or at least long-term) PFO closure.

The phrase "tissues adjacent a PFO," or simply "PFO tissues," for the purposes of this application, means any tissues in, around or in the vicinity of a PFO which may be used or manipulated to help close the PFO. For example, tissues adjacent a PFO include septum primum tissue, septum secundum tissue, atrial septal tissue lateral to the septum primum or septum secundum, tissue within the tunnel of the PFO, tissue on the right atrial surface or the left atrial surface of the atrial septum and the like. By "application or removal" of energy, it is meant that energy may be transferred either to or from PFO tissues. In various embodiments, any of a number of energy transfer devices and forms of energy may be used to provide such energy transfer. Types of energy used may include, for example, radiofrequency energy, cryogenic energy, laser energy, ultrasound energy, resistive heat energy, microwave energy and the like.

Application of energy to (or removal of energy from) tissues to substantially close the PFO acutely may sometimes be referred to as "tissue welding." Preferably, tissue welding methods of the present invention will be performed without using tissue soldering material or other foreign material. In some embodiments, however, it may be advantageous to use one or more solder materials. Various solders and other tissue soldering matrices are described more fully in U.S. patent application Ser. No. 10/665,974 which was previously incorporated by reference. Examples of tissue solders or adhesives which may be used include, but are not limited to, autologous blood, albumin, collagen, fibrin, cyanoacrylates, mussel byssus adhesives, polymer hot melt adhesives and the like.

In some embodiments of the present invention, devices and methods further provide for bringing tissues adjacent a PFO together (or "apposing" tissues). In various embodiments, tissues may be apposed before, during and/or after application or removal of energy to the tissues. Generally, energy application or removal will act to denature collagen in the PFO tissues. If the tissues are apposed before and/or during denaturation and/or while the collagen in the tissues is allowed to renature, the collagen in once-separated tissues binds together to bring the tissues together. Therefore, although not required, some embodiments of the invention include one or more devices for bringing (and possibly holding) tissues together before, during and/or after energy application or removal. Such devices include, for example, PFO tissue covering members, which may also be suction or vacuum application members, expandable members within the PFO tunnel, distal tip members for contacting a left atrial surface of PFO tissue and the like. By providing for substantial, acute closure of a PFO, devices and methods of the invention may be advantageous for preventing stroke, treating migraine headaches and/or preventing or treating other medical conditions caused or exacerbated by PFO.

In one aspect of the present invention, a method of treating a PFO in a heart involves advancing a catheter device to a position in the heart for treating the PFO and applying energy to the tissues with the catheter device to substantially close the PFO acutely. In some embodiments, as just mentioned, the method further includes bringing the tissues at least partially together, preferably using the catheter device but in some embodiments using a separate device. For example, in some embodiments the tissues are brought together before applying the energy. Optionally, the tissues may then be held together while applying the energy. In some embodiments, the tissues are held together after the energy has been applied as well. The method may also involve cooling the tissues after the energy has been applied.

Bringing the tissues at least partially together may be accomplished by any of a number of suitable devices and methods. In one embodiments, for example, the tissues are contacted with a tissue covering member adjacent a distal end of the catheter device. The tissue covering member may cause blood pressure in a left atrium of the heart to bring the tissues at least partially together. In some embodiments, the tissue covering member may be further used to apply vacuum force to the tissues.

Although the catheter device may be positioned in a number of different locations for treating a PFO, in some embodiments advancing the catheter involves positioning a distal end of the catheter in a right atrium of the heart. Advancing the catheter may also include advancement over a guide catheter or guidewire extending into the PFO. Optionally, the guide catheter or guidewire may extend through the PFO into a left atrium of the heart.

In some embodiments, the method further includes retracting a sheath portion of the guide catheter to expose an expanding member within the PFO, the exposed expanding member bringing the tissues adjacent the PFO at least partially together. Such an expanding member may provide lateral force to the tissues adjacent the PFO, for example, and in some embodiments will do so without extending into the left atrium. As is explained further below, such expanding members may comprise "fishmouth," two-pronged members in one embodiment, and may be constructed of shape memory materials, spring-loaded materials or the like. By spreading PFO tissues laterally between two prongs (for example), the tissues come together in the area between the prongs. Optionally, the method may also include contacting a left atrial surface of at least one of a septum primum and a septum secundum with a distal portion of the expanding member and retracting the expanding member to bring the tissues adjacent the PFO together. For example, the distal portion may contact the septum primum and pull it toward the right side of the heart, into contact with the septum secundum. At some point after the expanding member has been used to appose the tissues adjacent the PFO, it may be advantageous to retract the expanding member to a position within the guide catheter. For example, the expanding member may be retracted in some embodiments before removing the guide catheter through the main catheter device.

As mentioned, in some embodiments the catheter device may be advanced over a guidewire rather than a guide catheter. The guidewire typically extends through the PFO and may include an expanding portion along its length for expanding within the PFO. Optionally, the guidewire may extend into the left atrium, and the method may optionally include contacting a left atrial surface of at least one of a septum primum and a septum secundum with a distal portion of the guidewire and retracting the guidewire to bring the tissues adjacent the PFO together.

Any suitable type of energy may be applied to the PFO tissues to provide acute PFO closure. In some embodiments, for example, monopolar or bipolar radiofrequency energy is applied, while in alternative embodiments cryogenic, resistive heat, ultrasound, microwave, or laser energy, heat energy in the form of heated fluid such as saline, or the like may be applied. Energy may be applied by energizing a single conductive member of the catheter device or multiple conductive members, in various embodiments. Generally, any suitable devices for energy delivery are contemplated.

Some embodiments of the method may further involve monitoring an amount of energy applied to the tissues. For example, monitoring the energy may involve monitoring a temperature of the tissues, an impedance of the tissues and/or the like. Such a method may further involve determining when a sufficient amount of energy has been applied to the tissues to acutely close the PFO. Optionally, the method may also include discontinuing the application of energy when the sufficient amount of energy has been applied.

Any of the above methods may also involve directly visualizing the PFO and the adjacent tissues using at least one visualization device coupled with the catheter device. Such a visualization device may include a fiber optic device, an ultrasound device or any other suitable visualization device.

In another aspect of the invention, a method of treating a PFO in a heart involves advancing a catheter device to a position in the heart for treating the patent foramen ovale and removing energy from tissues adjacent the patent foramen ovale with the catheter device to substantially close the patent foramen ovale acutely. Removing energy from the tissues may be achieved using any suitable device(s), such as by contacting the tissues with one or more cryogenic energy members. Any of the additional or alternative method steps described above may be applied to this aspect of the invention.

In another aspect of the invention, apparatus for treating a PFO in a heart includes a catheter device having a proximal end and a distal end and at least one energy transmission member adjacent the distal end for applying energy to, or removing energy from, tissues adjacent a PFO to acutely close the PFO. Some embodiments further include at least one tissue apposition member adjacent the distal end for at least partially bringing the tissues together. In some embodiments, the tissue apposition member comprises a tissue covering member. The tissue covering member may have any suitable configuration and be constructed from any suitable material(s). In some embodiments, for example, the tissue covering member has a suction cup or cone shape.

In some embodiments, the tissue covering member fully covers the opening of the PFO to allow blood pressure in a left atrium of the heart to bring the tissues together. Additionally, the tissue covering member may comprise a suction member for applying vacuum force to the tissues to bring the tissues together. Optionally, the tissue covering member may be expandable from a first delivery dimension to a second treatment dimension. In some embodiments, the catheter further comprises a flexible isolation portion disposed between the tissue covering member and the catheter device to prevent unwanted movement of the tissue covering member during use. In some embodiments, the at least one energy transmission member is coupled with the tissue covering member.

Some embodiments of the apparatus further include a guide member for advancing through the PFO, with the catheter device being slidably disposed over the guide member. The guide member may include, for example a guide catheter and at least one expandable member disposed within the guide catheter, wherein the guide catheter is retractable to expose the expandable member to allow it to expand within the PFO. The expandable member, in turn, may have any suitable configuration, but in some embodiments it includes at least two members that expand apart to provide lateral force to the tissues adjacent the PFO, such as a "fishmouth" or two-prong expandable member. When exposed, the expanding member may also provide dilatory force to the tissues adjacent the PFO. To provide expandability, the expandable member may be made of shape memory material, may be spring loaded, and/or the like.

In alternative embodiments, the guide member may comprise a guidewire having an expandable portion along its length. For example, the expandable portion may be a divided portion, the divided portion comprising expandable shape memory material. Optionally, the guide member may include at least one tip for contacting a left atrial surface of the tissues adjacent the PFO. Such a tip may be conformable to the left atrial surface. The guide member may be retractable to engage the at least one tip with the left atrial surface.

In any of the above embodiments, one or more guide members, or component parts of a guide member, may act as one or more energy transmission members. In some embodiments, for example, an expanding member may act as a monopolar or bipolar radiofrequency electrode.

The at least one energy transmission member of the catheter device may comprise any suitable energy transmission device or combination of devices. For example, the transmission member may transmit radiofrequency energy, cryogenic energy, resistive heat energy, ultrasound energy, microwave energy, laser energy or any other form of energy for treating PFO tissues. In preferred embodiments, the energy transmission member comprises a monopolar or two bipolar radiofrequency transmission members. Such a transmission member, for example, may be curved to approximate the curvature of the PFO. In other embodiments, straight transmission members, mesh or braided transmission members, multiple pin-point transmission members or the like may be used.

In some embodiments, the energy transmission member(s) are coupled with the tissue apposition member. Thus, tissues may be brought into apposition and energy may be applied using the tissue apposition member. In some embodiments, energy transmission member is movable along at least part of a circumference of the at least one tissue apposition member. In alternative embodiments, the energy transmission member comprises a guide member for advancing through the PFO, with the catheter device being slidably disposed over the guide member. Again, the guide member typically includes at least one expandable portion for expanding within the PFO to at least partially bring together the tissues adjacent the PFO, and in some embodiments the expandable member acts as the energy transmission member(s). In still other embodiments, energy transmission members may be coupled with both the tissue apposition member and the guide member/expandable member.

Apparatus of the invention may further include at least one sensor coupled with the catheter device for sensing an amount of energy delivered to the tissues by the at least one energy transmission member. Sensors, for example, may be infrared sensors, thermistors, thermocouples or the like, though any sensors may be used. Optionally, a microprocessor may be coupled with the at least one sensor for processing sensed data to determine when the amount of delivered energy has reached a desired amount of energy.

These and other embodiments are described in further detail in the following description related to the appended drawing figures.

BRIEF DESCRIPTION OF THE DRAWING FIGURES

FIG. 10 illustrates a backstop device according to another embodiment of the present invention.

FIG. 11 illustrates a coil version of a backstop device according to another embodiment of the present invention.

FIG. 12 illustrates a balloon version of a backstop device according to another embodiment of the present invention.

DETAILED DESCRIPTION OF THE INVENTION

Devices and methods of the present invention generally provide for patent foramen ovale (PFO) treatment through application or removal of energy. Methods involve advancing a catheter device to a position in the heart for treating the PFO and applying energy to (or removing energy from) tissues adjacent a PFO to substantially close the PFO acutely. Terms such as "substantially," "acutely," and "tissues adjacent the PFO" are defined above in the Brief Summary of the Invention. Devices of the invention generally include a catheter device having a proximal end and a distal end and at least one energy transmission member adjacent the distal end for applying energy to or removing energy from tissues adjacent the PFO.

Figure 1:
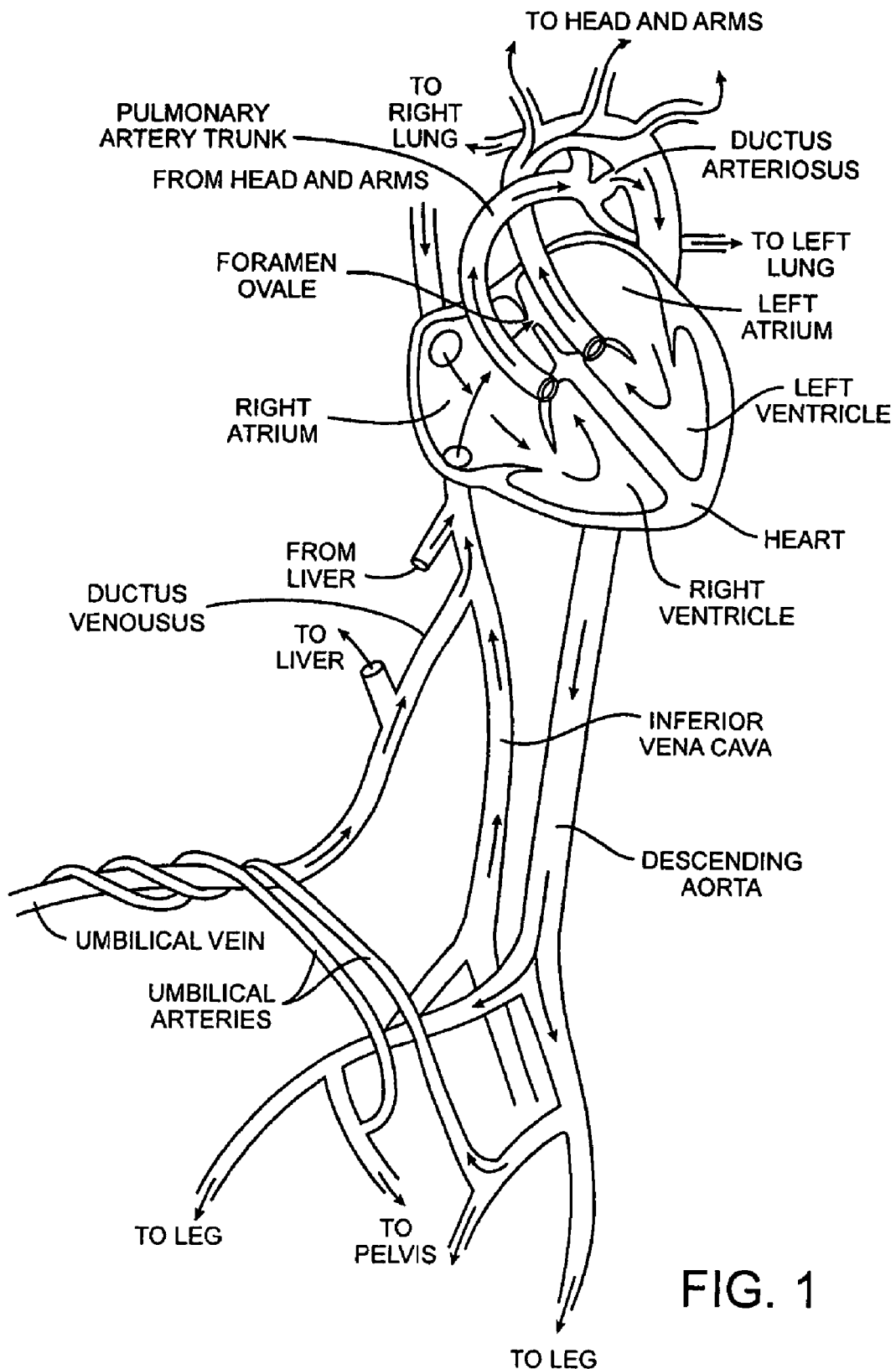
FIG. 1 is a diagram of the fetal circulation.

As mentioned above in the background section, FIG. 1 is a diagram of the fetal circulation. The foramen ovale is shown, with an arrow demonstrating that blood passes from the right atrium to the left atrium in the fetus. After birth, if the foramen ovale fails to close (thus becoming a PFO), blood may travel from the right atrium to the left atrium or vice versa, causing increased risk of stroke, migraine and possibly other adverse health conditions, as discussed above.

Figure 2:
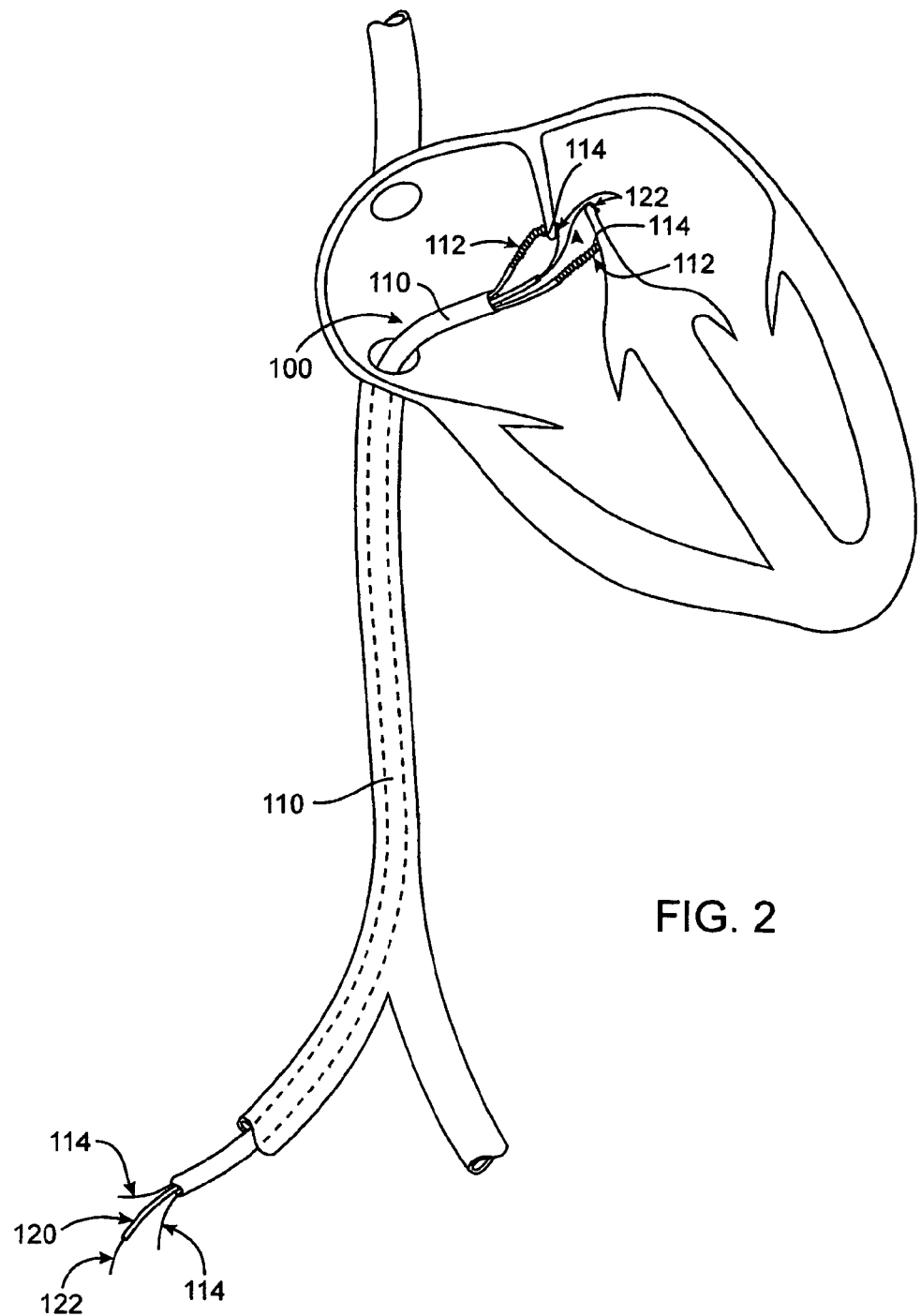
FIG. 2 is a diagram of a catheter apparatus according to an embodiment of the present invention, having a conductive element and closure device, the catheter passing through the inferior vena cava and right atrium and through the PFO.

With reference to FIG. 2, one embodiment of a PFO-treatment apparatus 100 may be advanced through the vasculature of a patient to a position in the heart for treating a PFO. In this embodiment, apparatus 100 includes an elongate catheter device 110 having one or more tissue apposition members 112 and one or more energy transmission members 114 at or near its distal end. Optionally, catheter device 110 may be slidably disposed over a guide member 120, such as a guide catheter (as in FIG. 1), a guidewire, or the like. Guide member 120 may include, for example, one or more expanding members 122 or other similar devices for deploying within the PFO to help appose the adjacent tissues. In some embodiments, as described further below, expanding members 122 may comprise (or be coupled with) one or more energy transmission members 114. Generally, apparatus 100 may be used to bring together tissues surrounding and/or adjacent the PFO and to transmit energy to the tissues to close the PFO.

Although the embodiment in FIG. 2 and many of the embodiments described below include one or more tissue apposition members, devices of the present invention do not require such members. In some embodiments, as mentioned above and as set forth in the claims, devices may include a catheter device having one or more energy transmission members for applying or removing energy, without any components designed for bringing the tissues together. Therefore, although much of the following discussion focuses on embodiments including tissue apposition members and the like, such members are not required.

Figures 3, 3A, 3B:
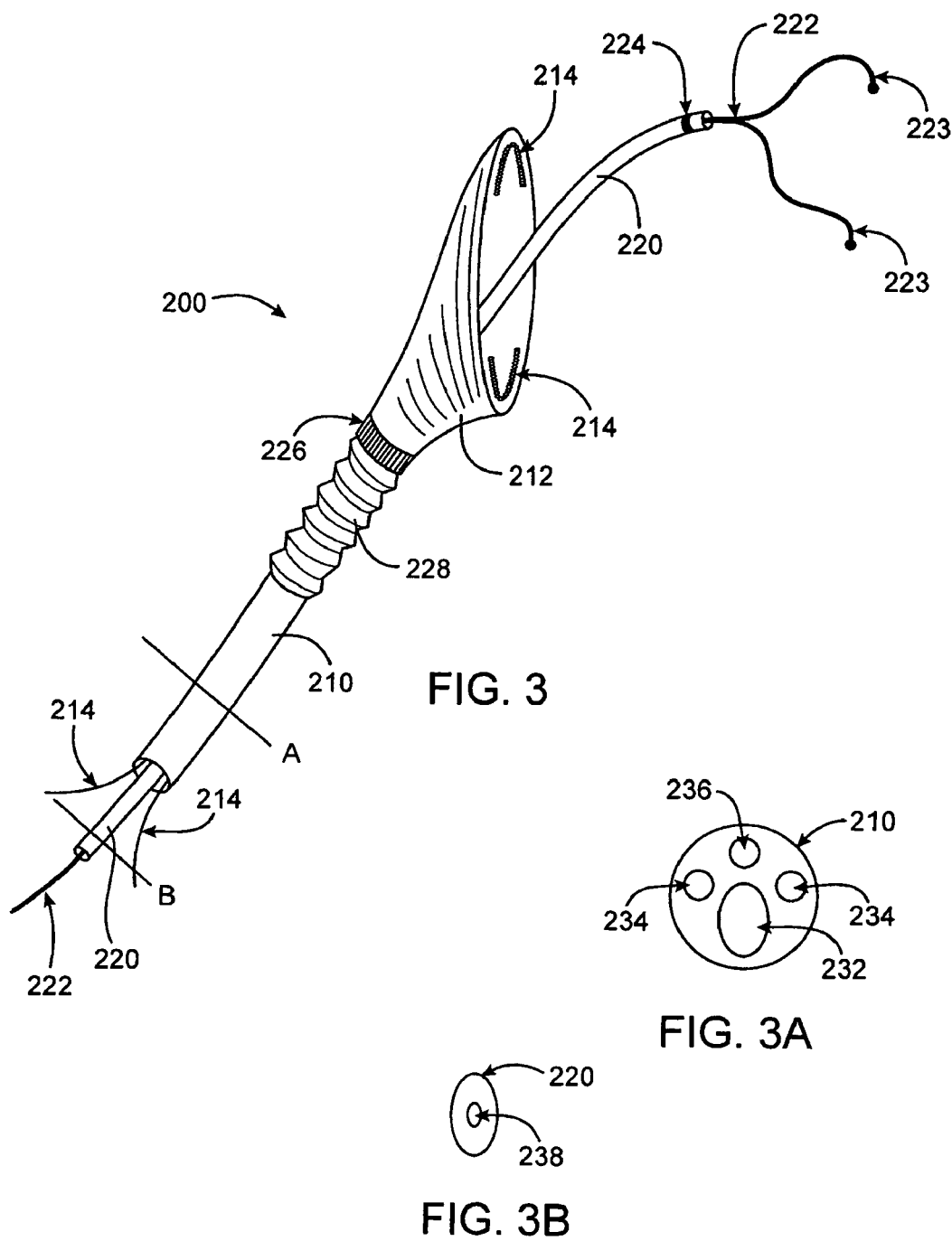
FIG. 3 is a perspective view of a catheter apparatus according to an embodiment of the present invention.
FIGS. 3A and 3B are cross-sectional views of the catheter apparatus in FIG. 3.

Referring now to FIG. 3, one embodiment of a PFO-treatment apparatus 200 suitably includes a catheter device 210 coupled with a tissue apposition member 212 at its distal end. One or more energy transmission members 214 may be disposed through or within catheter device 210 and/or coupled with tissue apposition member 212. In some embodiments, catheter device 210 is slidably disposed over a guide catheter 220. Guide catheter 220 may contain one or more expandable elements 222, such as a guide wire or the like. One or more radiopaque markers 224, 226 may be included on catheter device 210, guide catheter 220 or both. Catheter device 210 may also include an isolation portion 228 for helping to stabilize tissue apposition member 212 during use, so that it is not caused to move due to the flexibility of catheter device 210.

FIGS. 3A and 3B show cross-sectional views of apparatus 200 from the perspective of lines A and B in FIG. 3, respectively. In FIG. 3A, catheter device 210 is shown, having a guide catheter lumen 232, two energy transmission member lumens 234 and a vacuum lumen 236. As shown in FIG. 3B, guide catheter 220 includes an expandable element lumen 238. Guide catheter lumen 232 may sometimes be configured with an inner diameter (or "profile") that is shaped (or "keyed") to allow guide catheter 220 to pass easily through lumen 232. This feature is demonstrated in FIGS. 3A and 3B, where guide catheter 220 and guide catheter lumen 232 each have an ovoid shape.

In general, catheter device 210 comprises an elongate, flexible catheter which may be advanced through the vasculature of a patient to a position in the heart for treating a PFO. Thus, catheter device 210 may have any suitable length, diameter, cross-sectional profile and the like, and may be constructed of any suitable material. Tissue apposition member 212 (or multiple tissue apposition members in some embodiments) is disposed at or near the distal end of catheter device 210. Although many different types of devices may be used to bring tissues of the PFO together, in one embodiment (shown in FIG. 2) tissue apposition member 212 comprises a PFO-covering member. PFO-covering tissue apposition member 212 may be positioned to contact adjacent PFO tissues to fully cover, or block, the opening of the PFO. This blocking of the PFO may prevent right-to-left shunting of blood and may allow blood pressure in the left atrium to bring the septum primum and septum secundum at least partially together to close the PFO. Therefore, simply by forming a seal or blockage over the PFO, tissue apposition member 212 may help bring the PFO tissues together to assist in PFO closure.

In this and other embodiments, tissue apposition member 212 may also include one or more vacuum members for applying vacuum to the PFO tissues. In one embodiment, for example, suction lumen 236 (FIG. 3A) may extend from the proximal end to the distal end of catheter device 210, opening into one or more vacuum-application apertures at the distal end of tissue apposition member 212. The vacuum-application aperture(s) may have any suitable configuration, such as a continuous aperture encircling tissue apposition member 212, multiple apertures encircling tissue apposition member 212 or in any other suitable configuration at or near its distal end, or the like. In still another embodiment, vacuum may be applied via a large, central lumen in tissue apposition member 212. In any case, vacuum force may be used to bring PFO tissues together and/or to secure tissue apposition member 212 and thus catheter device 210 to the PFO tissues.

Tissue apposition member 212, especially when configured as a PFO-covering member, may be collapsible/expandable to facilitate advancement and delivery of catheter device 210. For example, tissue apposition member 212 may comprise a collapsible polymeric cover disposed over an expandable/collapsible frame. In other embodiments, tissue apposition member 212 may be constructed of a shape memory material, such as nitinol or another shape memory metal, spring stainless steel or the like, to allow catheter device 210 to be delivered through vasculature and then allow tissue apposition member 212 to expand to contact and appose the PFO tissues. In some embodiments, catheter device 210 and tissue apposition member 212 may be delivered to a location for PFO treatment through an introducer sheath. To further enhance the use of apparatus 200, an angle between catheter device 210 and tissue apposition member 212 may be selected to approximate a convenient angle for delivery and/or deployment. In one embodiment, for example, the angle between catheter device 210 and tissue apposition member 212 may approximate the angle between the inferior vena cava and the interatrial septum. Any other configuration, combination of angles and the like is contemplated, however. In some embodiments, for example, direct steering of the angle of tissue apposition member 212 relative to catheter device 210 may be employed to enhance delivery of catheter device 210 to a treatment site.

To further facilitate use of apparatus 200, catheter device 210 may include one or more radiopaque markers 226 for facilitating visualization of the device 210. Catheter device 210 may also include a "flexible isolation portion" 228, which in some embodiments comprises a rigid but shapeable portion disposed toward the distal end of catheter device 210, between tissue apposition member 212 and the generally flexible proximal portion of catheter device 210. Flexible isolation portion 228 may help to isolate tissue apposition member 212 from some or all movement experienced by the more flexible, proximal portion of catheter device 210, thus allowing a PFO treatment procedure to be performed without significant movement of tissue apposition member 212. In other embodiments, flexible isolation portion 228 may be more flexible than the more proximal portion of catheter device 210, thus enhancing maneuverability, shapability or the like of the position of tissue apposition member 212 relative to the more proximal portion.

Energy transmission members 214 may comprise any of a number of devices and may transmit any suitable type of energy for closing a PFO. Some types of energy which may be used, for example, include radiofrequency, cryogenic, resistive heat, ultrasound, microwave and laser energy. Radiofrequency energy transmission members 214 may be either monopolar or bipolar, with monopolar catheter devices also including a grounding member. Energy transmission members 214 may have any suitable configuration. For example, they may have a curved shape to approximate a radius of curvature of the PFO, as shown in FIG. 3, or they may be configured as points for spot-welding the PFO tissues, as a circular member for welding around the circumference of PFO tissues, as one or more mesh or braided members disposed within the orifice of tissue apposition member 212 or the like. In some embodiments, energy transmission members 214 are fixedly coupled with tissue apposition member 212, while in other embodiments energy transmission members 214 are movable within tissue apposition member, for example to move about the circumference of the PFO to weld PFO tissues at multiple locations.

As mentioned earlier, the phrase "tissue welding" herein is used to mean application of energy to (or removal of energy from) PFO tissues to substantially and acutely close the PFO. Energy transmission members 214 generally provide for transfer of energy to or from PFO tissues to denature collagen in the tissues, and when the collagen is allowed to renature, with the tissues apposed, the once separated tissues bind together to form a stable tissue bridge. This stable tissue bridge substantially and acutely closes the PFO, preferably permanently. PFO tissues may, in some embodiments, be brought and held together by one or more tissue apposition members 212. Energy transmission members 214 provide sufficient energy transfer, for a sufficient time, to weld the tissues. The time span of energy transmission may be, for example, from about 0.5 seconds to about 15 minutes, and more preferably from about 30 seconds to about 5 minutes. Energy transmission, in some embodiments, may be from about 0.5 Watts to about 100 Watts, and more preferably from about 2 Watts to about 20 Watts. Any other suitable energy and timing combination may also be used. In one experimental example, a PFO in a section of pig heart tissue used ex-vivo in a flowing saline test fixture was closed by applying suction to appose the PFO tissues and applying RF energy at approximately 25 watts for 7 minutes. RF energy application was then discontinued, but suction was continued for an additional 1 minute to keep tissues in apposition while the tissue cooled, to allow collagen in the tissues to reorganize and bind together to form a stable tissue bridge. Many other energy amounts, energy application times, tissue apposition times and the like are contemplated, however.

Although any type of energy may be transmitted by energy transmission members 214, some embodiments will make use of monopolar or bipolar radiofrequency (RF) energy. Devices may use monopolar radiofrequency energy, for example, wherein energy is applied simultaneously to all conductive elements, completing the circuit through an external ground pad affixed to the skin of the patient. Alternatively, bipolar energy may be applied to all conductive elements simultaneously, and the circuit completed through a ground element incorporated elsewhere on apparatus 200. Further embodiments may include applying bipolar energy between two or more energy transmission members 214, which are electrically isolated from one another within catheter device 210.

Control systems coupled with energy transmission members 214 or tissue apposition member 212, or otherwise disposed within apparatus 200, may sense an amount of energy delivered to PFO tissues and, optionally, may automatically stop energy delivery upon detecting a change in condition of energy delivery, for instance an increase in electrical resistance or impedance in PFO tissues or in apparatus 200, an increased energy draw from the treatment apparatus, and/or the like. In some embodiments, energy delivery may be automatically stopped when an amount of delivered energy reaches a desired level, such as an amount of energy sufficient to substantially close the PFO. The amount of delivered energy may be monitored by any suitable method, such as monitoring temperature or impedance in PFO tissues or the like. In some embodiments, one or more sensors coupled with tissue apposition member 212, energy transmission members 214, or any other part of apparatus 200 may be used for monitoring such indicia. Examples of sensor devices include but are not limited to infrared sensing devices, thermistors and thermocouples. A control system may also include a microprocessor coupled with the sensors to determine when a desired amount of energy has been delivered and/or to automatically stop energy transmission. In alternative embodiments, a microprocessor may be included in apparatus 200 which can sense, monitor and control energy delivery, thus not requiring separate sensors.

With continued reference to FIG. 3, some embodiments of apparatus 200 include guide catheter 220, or an alternative guide member as discussed further below. Guide catheter 220 is generally a flexible catheter along which catheter device 210 may be slidably advanced to a position for PFO treatment. Guide catheter 210 is configured to fit at least partially within a PFO and optionally through a PFO into the left atrium of the heart. Optionally, one or more radiopaque markers 224 may be included on guide catheter.

Guide catheter 220 may contain one or more expandable members 222 or other similar devices for expanding within the PFO to help bring the PFO tissues together, anchor catheter device to the PFO tissues, or both. As shown in FIG. 3, for example, a "fish mouth" or two-prong expandable member 222 may be deployed within a PFO. When the two arms of the fish mouth separate, PFO-adjacent tissues are stretched laterally such that they tend to come together in the middle. In some embodiments, expandable members 222 may assist in PFO tissue apposition either while extending into the left atrium, while in other embodiments expandable members 22 do not extend into the left atrium.

Expandable member 222 may have any suitable configuration and may be constructed from any suitable materials. For example, expandable member 222 may be spring loaded, made of shape memory material, such as nitinol or spring stainless steel or the like. Alternatively, expandable member 222 may be expanded mechanically by one or more expansion members coupled with expandable member 222 and controlled via an actuator at the proximal end of guide catheter 220. During delivery of guide catheter 220, expandable member 222 reside within guide catheter 220. Guide catheter 220 may then be withdrawn to deploy expandable member 222 either within the PFO or within the left atrium to be drawn back into the PFO. In some embodiments, expandable member 222 has one or more pre-shaped or shapeable distal tips 223. Tips 223 may be used, for example, to help locate and cross the PFO. Tips 223 may also be used to contact a left atrial surface of the septum primum or other PFO tissue, so that when the expandable member 222 is pulled proximally tips 223 help bring the PFO tissues together and/or anchor apparatus 200.

In some embodiments, one or more expandable members 222 may include or be coupled with one or more energy transmission members. For example, expandable member 222 may include one or more radiofrequency transmission members for monopolar or bipolar RF transmission. A fish mouth expandable member 222, for example, may include a bipolar RF transmission member on each prong of the fish mouth. In some embodiments, energy transmission members may be included in or coupled with both expandable member 222 and tissue apposition member 212. In any such embodiments, some portions of the energy transmission member(s) may be insulated, to prevent unwanted energy transmission to tissues. For example, in some embodiments a distal tip extending to contact a left atrial surface of PFO tissues may be insulated to prevent energy transmission from the tip.

Figure 4:
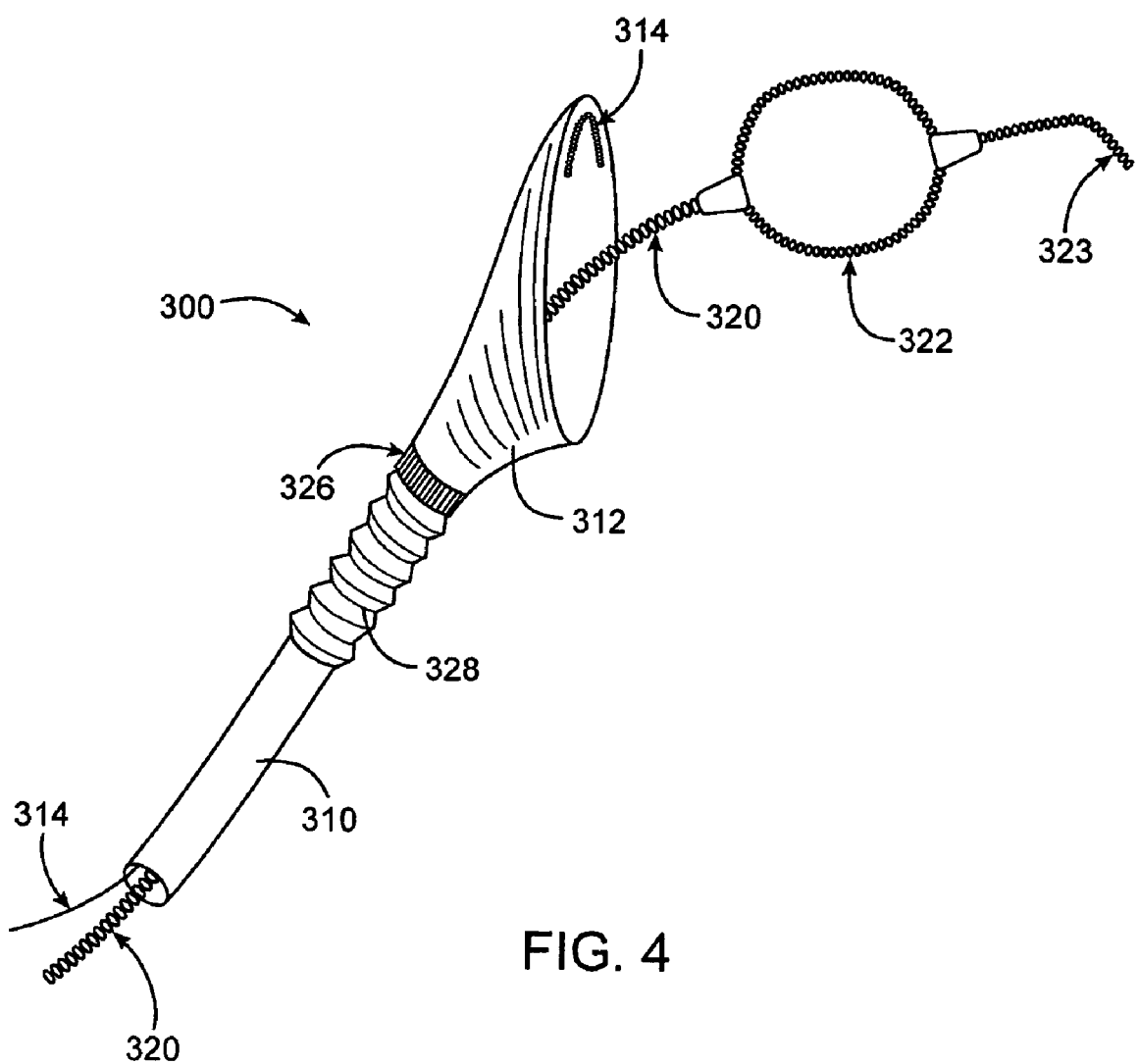
FIG. 4 is a perspective view of a catheter apparatus according to another embodiment of the present invention.

Referring now to FIG. 4, an alternative embodiment of a PFO-treatment apparatus 300 suitably includes a catheter device 310 having a tissue apposition member 312, radiopaque marker 326 and flexible isolation portion 328. For exemplary purposes only, this embodiment is shown having one energy transmission member 314, such as a monopolar RF transmission member. As shown, apparatus 300 may also include a guidewire 320, over which catheter device 310 may be advanced. Guidewire 320 includes a split, expandable portion 322, which may be released from catheter device 310 to expand within a PFO to bring PFO tissues together. Guidewire 320 also suitably includes a distal tip 323 for locating and crossing a PFO and/or for contacting a left atrial surface of the septum primum or other PFO tissue.

Apparatus 300 of FIG. 4 may include any of the features described above in relation to FIG. 3. In the embodiment in FIG. 4, apparatus 300 does not include a guide catheter, but instead includes guidewire 320. Guidewire 320 may serve many or all of the functions of the guide catheter and expanding member described above in reference to FIG. 3. Split portion 322 of guidewire 320 may be constructed of shape memory material or other suitable materials to allow it to expand when released from catheter device 310. Additionally, split portion 322 may include or be coupled with one or more energy transmission members instead of or in addition for energy transmission member(s) 314 coupled with tissue apposition member 312. Guidewire 320 may also include one or more distal tips 323, which again may be used to locate and cross a PFO and/or to help appose PFO tissues. In some embodiments, tip 323 may also include or be coupled with one or more energy transmission members.

Figure 5:
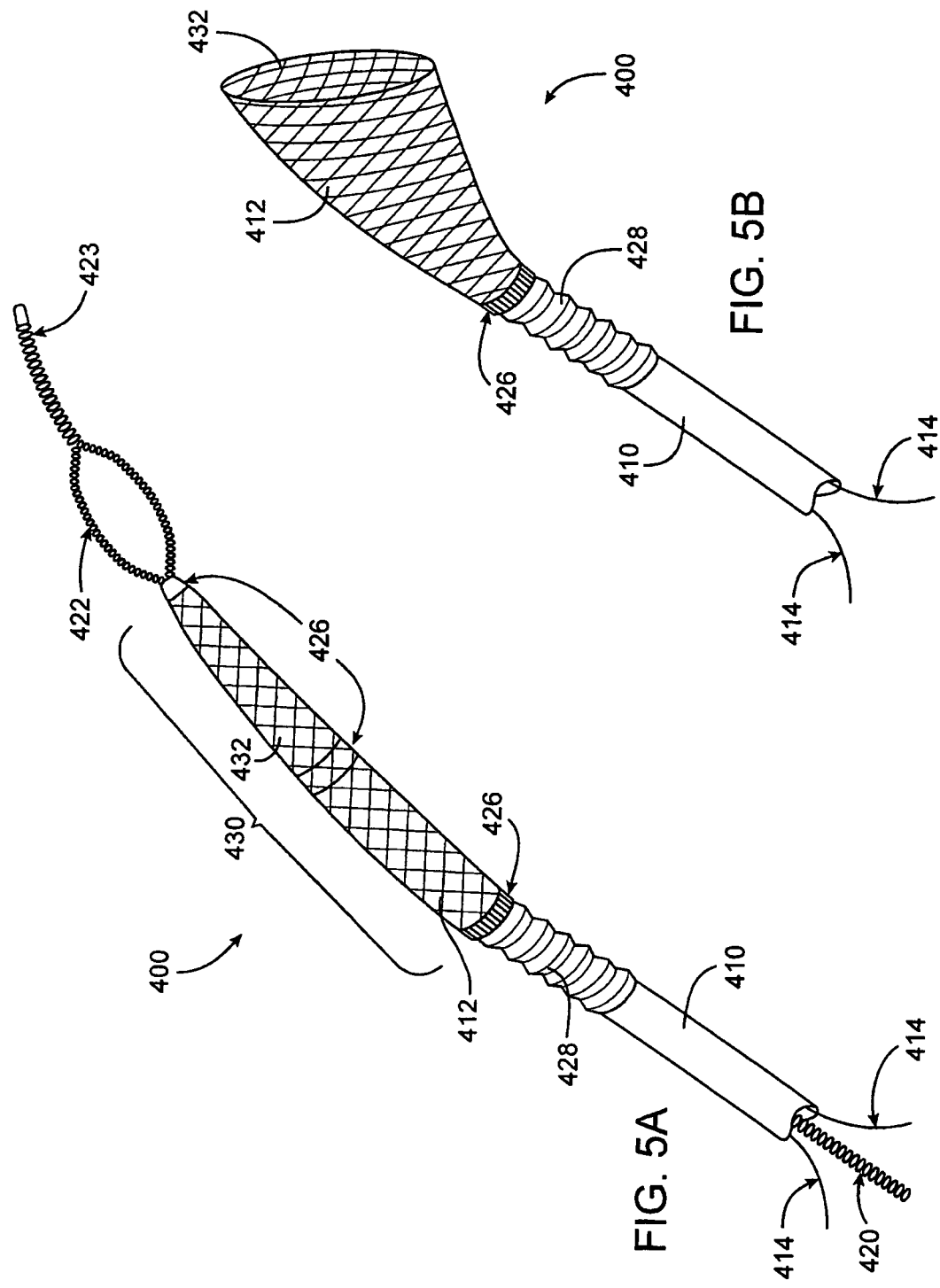
FIGS. 5A and 5B are perspective views of a catheter apparatus according to another embodiment of the present invention.

Referring now to FIGS. 5A and 5B, another embodiment of a PFO-treatment apparatus 400 suitably includes a catheter device 410 having a tissue apposition member 412, radiopaque markers 426 and flexible isolation portion 428. As shown, apparatus 400 may also include a guidewire 420, over which catheter device 410 may be advanced. Guidewire 420 includes a split, expandable portion 422, which may be released from catheter device 410 to expand within a PFO to bring PFO tissues together. Guidewire 420 also suitably includes a distal tip 423 for helping locate and cross the PFO and/or for contacting a left atrial surface of the septum primum or other PFO tissue to help bring the PFO tissues together. In this embodiment, catheter device 410 also includes a braided portion 430 which includes the proximally-disposed tissue apposition member 412 and a more distal energy transmission portion 432, the latter of which is coupled with energy transmission members 414. Tissue apposition member 412 and energy transmission portion 432 may be a unitary braided member, with tissue apposition member 412 configured to cover energy transmission portion 432 in a retracted position and to provide vacuum force application.

In use, catheter device 410 is typically advanced over guidewire 420 to a treatment location. Split portion 422 and optionally distal tip 423 are then used to help appose the tissues adjacent the PFO. Before, during or after retraction of guidewire 420, energy transmission portion 432 is retracted into tissue apposition member 412. PFO tissue is then brought together using tissue apposition member 412, and energy is transmitted to the tissues using energy transmission portion 432. In some embodiments, tissue apposition member 412 provides for application of vacuum energy to the tissues to suction the tissues at least partially into tissue apposition member 412, thus enhancing contact of the tissues with energy transmission portion 432. Energy transmission portion 432 may comprise, for example an electrode mesh material, while tissue apposition member 412 may comprise an elastic coated mesh or other material. Again, any features described above in reference to other embodiments may be applied to the embodiment shown in FIGS. 5A and 5B.

Figure 6:
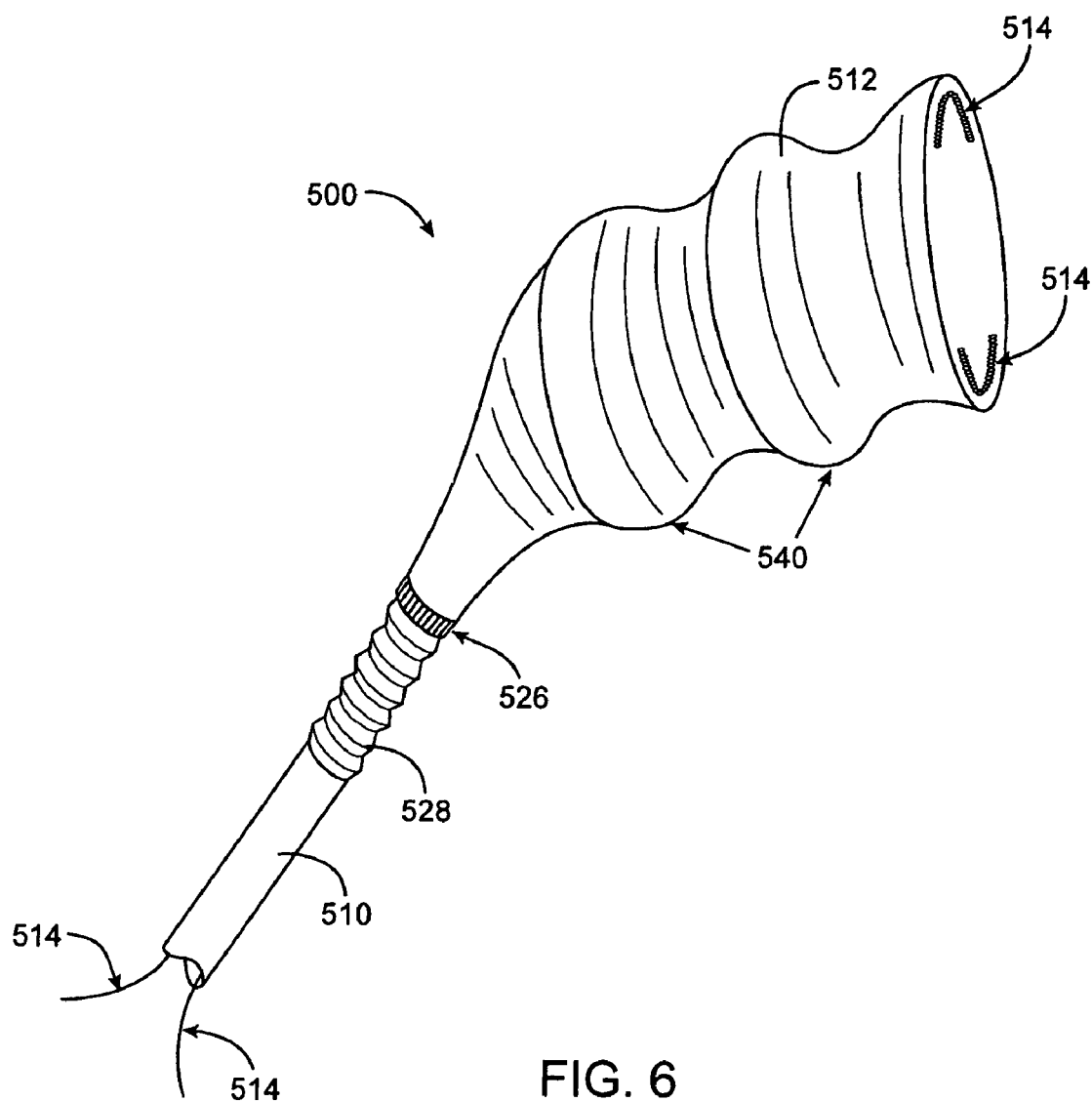
FIG. 6 is a perspective view of a catheter apparatus according to another embodiment of the present invention.

With reference now to FIG. 6, another embodiment of a PFO-treatment apparatus 500 suitably includes a catheter device 510 having a tissue apposition member 512, energy transmission members 514, radiopaque marker 526 and flexible isolation portion 528. For simplicity, apparatus 500 is shown without a guide catheter or guidewire, though either may be included. In this embodiment, tissue apposition member 512 includes ribs or "bellows" 540 to facilitate placement and/or alignment of tissue apposition member 512 relative to the septal wall tissues to be treated and/or to enhance adherence of apparatus 500 to the septal wall. For example, ribs 540 may allow catheter device 510 to move relatively freely relative to tissue apposition member 512, without displacing tissue apposition member 512 from the PFO tissues.

Figure 7:
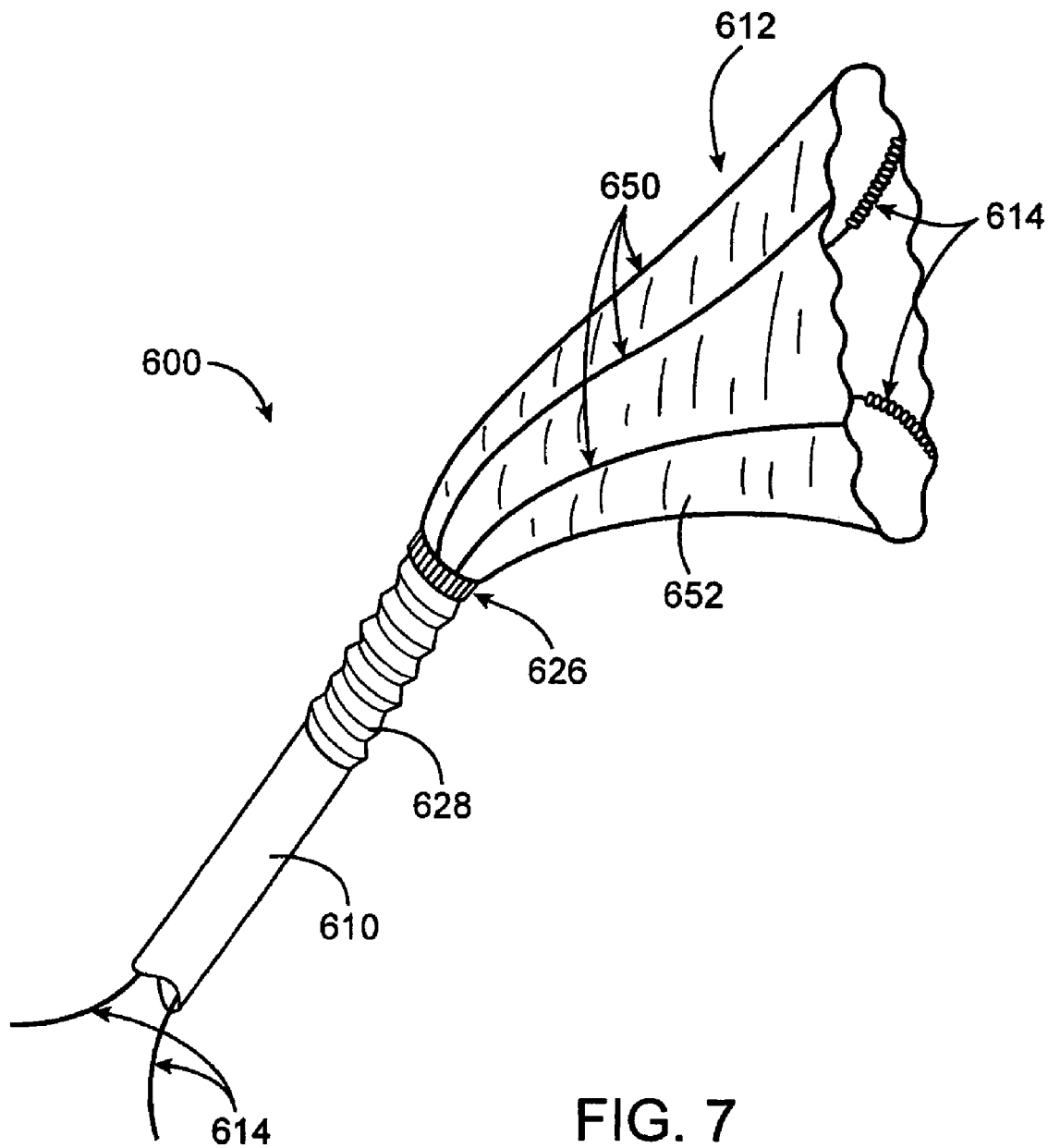
FIG. 7 is a perspective view of a catheter apparatus according to another embodiment of the present invention.

Referring now to FIG. 7, another embodiment of a PFO-treatment apparatus 600 suitably includes a catheter device 610 having a tissue apposition member 612, energy transmission members 614, radiopaque marker 626 and flexible isolation portion 628. Apparatus 600 is shown without a guide catheter or guidewire, though either may be included. In this embodiment, tissue apposition member 612 includes multiple struts 650 covered by a covering 652, which may comprise a polymeric covering or any other suitable material. Struts 650 may be self-expanding or may open via a mechanical opening actuator coupled with struts 650, such as opening apparatus used to open an umbrella. Energy transmission members 614 are coupled with self-expanding struts 650 on the internal surface of tissue apposition member 612, so as to contact PFO tissue that is pulled within tissue apposition member 612, such as by applied vacuum force and/or by blood pressure from the left atrium.

FIGS. 8A-8E demonstrate a method for treating a PFO according to one embodiment of the present invention. It should be emphasized that this is merely one possible embodiment, and that many alternative methods are contemplated. For example, steps may be modified, repeated, added or deleted from the method, the order of steps may be changed, and/or the like, without departing from the scope of the invention as defined by the appended claims. Therefore, the foregoing description should not be interpreted to limit the scope of the invention in any way.

Figure 8A:
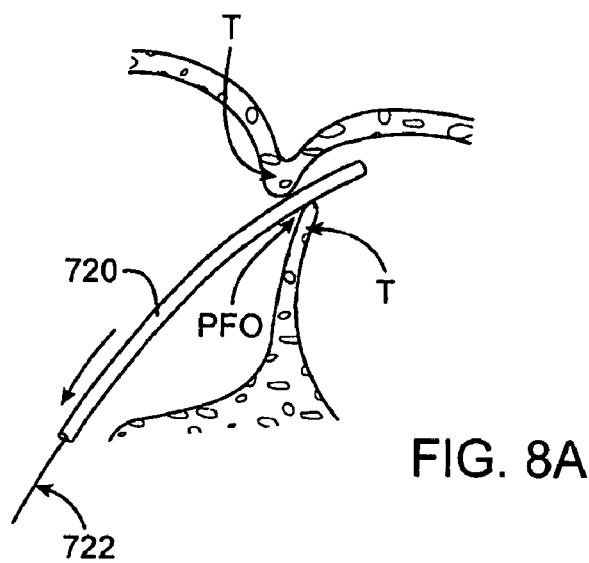
FIGS. 8A-8E demonstrate a method for treating a PFO using a catheter apparatus according to an embodiment of the present invention.
Figure 8B:
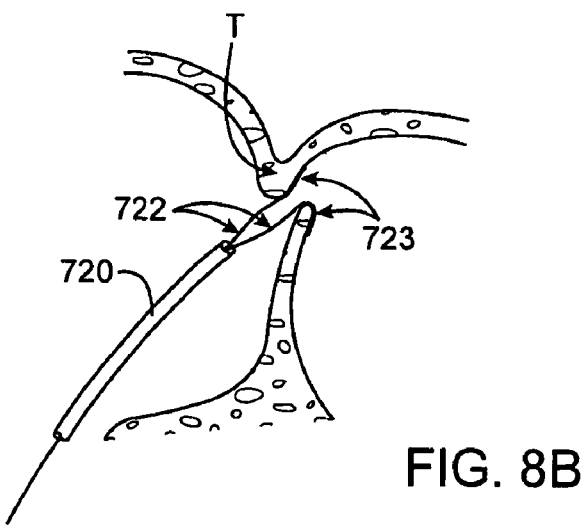

That being said, in one embodiment, a PFO treatment method includes advancing a guide catheter 720 through the PFO, between tissues T adjacent the PFO, the guide catheter 720 containing an expandable member (FIG. 8A). Guide catheter 720 is then retracted (proximally pointing arrow) to expose expanding member 722 (FIG. 8B). Expanding member 722 may be exposed/expanded within the PFO, or may alternatively be exposed/expanded within the left atrium and pulled back into the tunnel of the PFO. Expanding member 722 may also include one or more distal tips 723, which may help to locate the PFO, cross the PFO, appose the tissues T and/or to anchor guide catheter 720 to the tissues T.

Figure 8C:
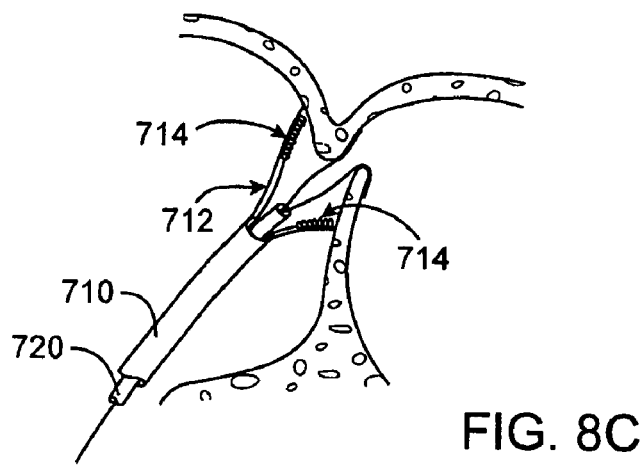
Figure 8D:
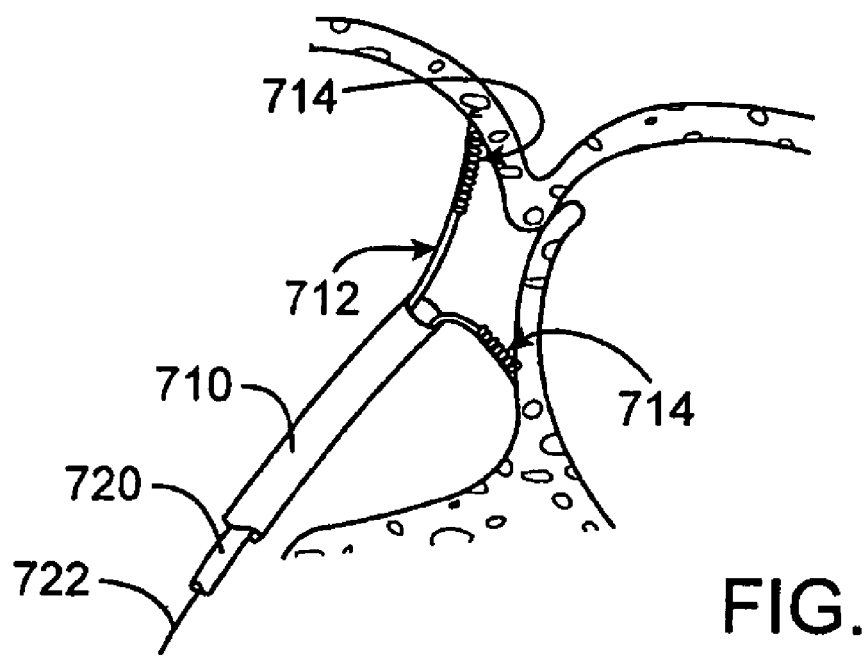
Figure 8E:
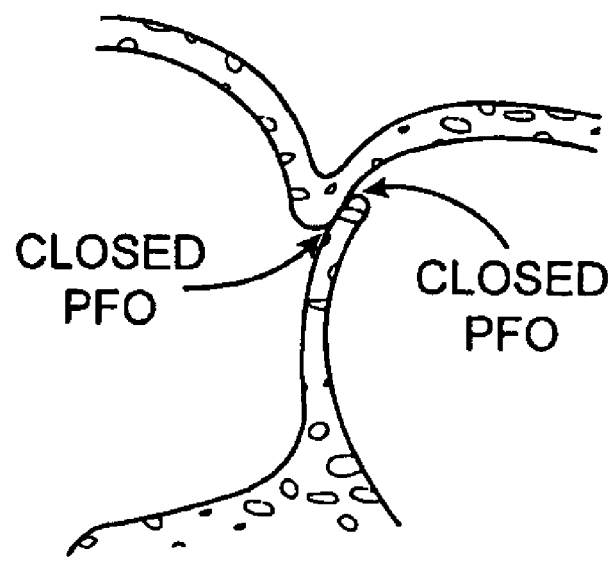

Once guide catheter 720 is in place and expandable member 722 is deployed, catheter device 710 may be advanced over guide catheter 720 to a position for treatment of the PFO (FIG. 8C). Catheter device 710 typically includes a tissue apposition member 712 (shown here in cross-section for clarity) and one or more energy transmission members 714. Suction may be applied using tissue apposition member 712, left atrial pressure may be used, or both, to bring tissues T adjacent the PFO together (FIG. 8D). Once tissue apposition member 712 is placed and/or activated, guide catheter 720 and expandable member 722 may be removed through catheter device 710, leaving the tissues T apposed and catheter device in place, as in FIG. 8D. Alternatively, guide catheter 720 and expandable member 722 may be left in place during a first welding to close the majority of the PFO and then removed. The small patent portions of the PFO remaining after the guide catheter 720 and expandable member 722 are removed may then be closed by a second weld or may be left open and allowed to close via healing or scarring. Tissue apposition member 712 may be used to hold tissues T together before, during and/or after energy transmission members 714 weld the tissues T together. Such holding of the tissues together and application of energy to weld the tissues may be performed for any suitable time, such as for less than one second to many minutes. Once a sufficient amount of energy has been applied to the tissues T to acutely close the PFO, catheter device 710 is removed, leaving a closed PFO, as in FIG. 8E.

Figure 9A:
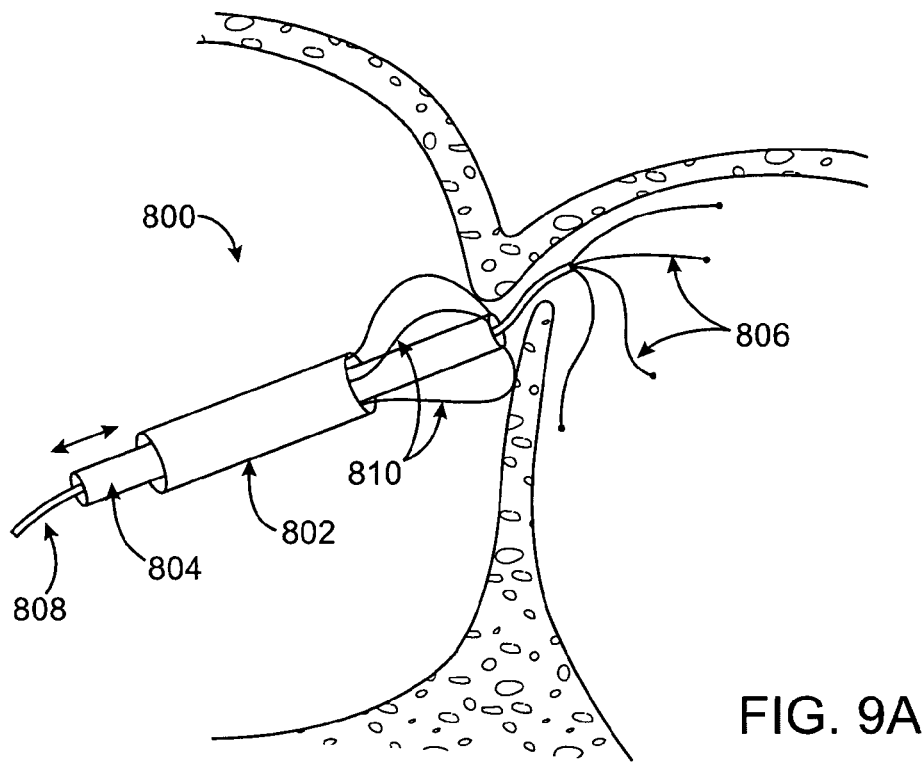
FIGS. 9A-9B illustrate a catheter apparatus including a backstop and inflatable member for treating a PFO according to one embodiment of the present invention.
Figure 9B:
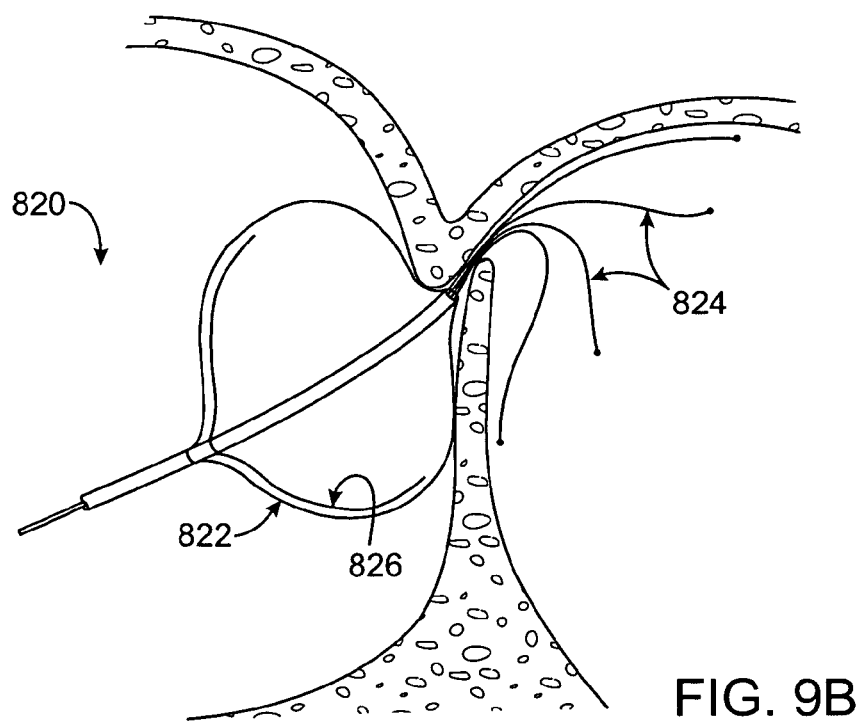

Apparatus and methods according to the present invention may rely on energy, in various forms, to seal the PFO, either with or without an associated implant device. As an alternative to implant-based devices, systems according to the present invention can function to weld the PFO closed with no implant left behind. As illustrated in FIGS. 9A and 9B, in some embodiments, a backstop and energy delivery catheter are placed in contact with the PFO, and energy is delivered to disrupt the collagen matrix of the primum and secundum to cause fusion of the two parts of the PFO. Energy used can be monopolar or biopolar RF (in which case the backstop acts as energy return), ultrasound, laser, microwave, or resistance heating. Protein solder may be introduced to facilitate the weld.

Referring to FIG. 9A, one embodiment of a backstop catheter device 800 for treating a PFO may include an outer catheter element 802, an inner catheter element 804, a backstop 806 coupled with a portion 808 extending through the inner shaft 804, and energy delivery arms 810. Energy delivery arms 810 can include ultrasound transducers, microwave antennae, or RF electrodes. The backstop catheter device 800 is advanced through the PFO and used to help advance an energy delivery catheter to the right atrial side of the PFO. Relative translation of an inner 804 and outer catheter element 802 deploy a set of arms 810 which carry the energy delivery elements. The energy delivered breaks down the collagen in each part of the PFO, and allows the tissues to be welded together. The energy delivered could take the form of RF, microwave, or ultrasound. RF energy can either be monopolar, in which the backstop 806 is electrically insulated such that it is not part of the energy delivery path, or bipolar, in which case the backstop 806 acts as the energy return electrode. If desired, the inner catheter 804 of the energy delivery catheter 800 can be used to infuse liquid albumin to act as a protein solder for the system. Alternatively, the shaft of the backstop 806 could be covered with a tube of solid or braided material made of, or soaked in, a tissue solder. After delivery of the energy and activation and bonding of the tissue solder to the PFO walls, the backstop 806 is withdrawn through the PFO and the entire system is withdrawn.

As illustrated in FIG. 9B, in another embodiment, a catheter device 820 can include an expandable balloon member 822 and an expandable backstop 824. The balloon catheter 820 can be outfitted with sections 826 of piezo film/foil which can be driven electrically to produce an ultrasound signal to heat and seal a PFO. The balloon member 822 and expandable backstop 824 are used to position the catheter device 820 in the desired location and energy is then applied via the piezo film/foil 826 for treating the PFO.

Variations of a backstop device according to the present invention are illustrated in FIGS. 10 through 13. Referring to FIG. 10, a backstop device 830 can have an inferior bias to preferentially engage the primum without interfering with the left atrial wall. Embodiments of the backstop device 830 are shown including prongs 832 and wire loops 834.

Referring to FIG. 11, a backstop device can include a coiled version 840, where a gidewire reforms into a coil 842 when introduced into the left atrium. The coil can be reverse-bias coil, so traction causes a former seat, or inferior-bias coil 846, so there is less contact with the left atrial wall superiorly. A flat coil version 848 of a backstop device is also shown.

FIG. 12 shows a balloon version backstop device, with a soft, low-pressure balloon 852 and a fixed wire 854. The balloon 854 can be concentric to the shaft 856, or inferior-biased for clearance. The inferior-bias balloon 858 preferentially engages the primum without hitting the left atrial wall. The device can be fixed-wire, over-the-wire, or tip-mounted with no central lumen for a guide wire or for inflation only.

Figure 13A:
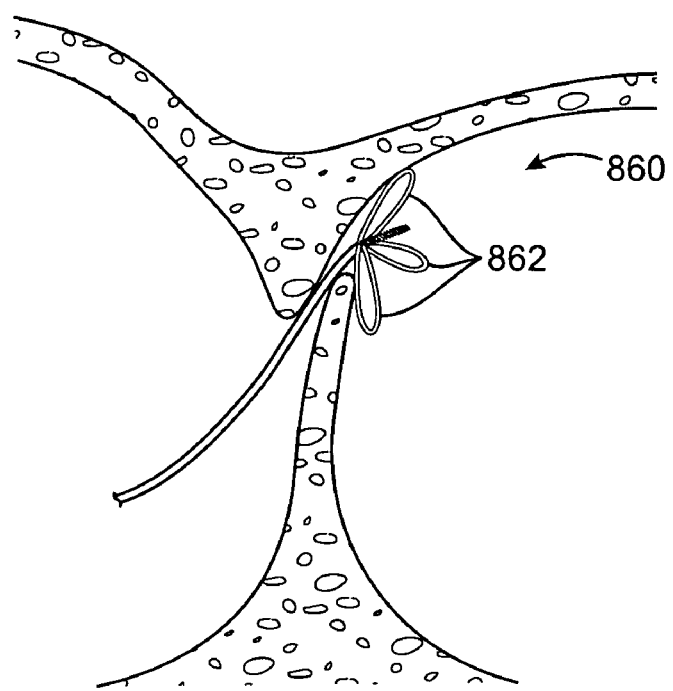
FIG. 13A-13C illustrates a flower petal version of a backstop device according to another embodiment of the present invention.
Figure 13B:
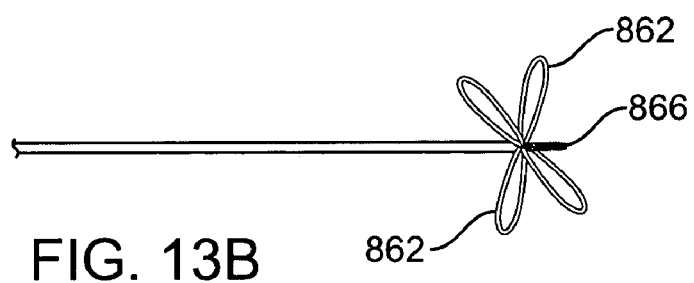
Figure 13C:

FIGS. 13A through 13C show a backstop device 860 with a normally-open flower petal 862, where nitinol petals 862 are biased open, and attached proximal to an outer catheter 864, distal to a core wire 866. Translation of the core wire 866 opens and closes the petals 862. The petals 862 are shown attached to the core wire 866 and the outer catheter 864 (FIG. 13B). The core wire 866 is advanced to collapse the petals 862 (FIG. 13C).

As mentioned above, the foregoing method may be altered in any number of ways without departing from the scope of the invention. In some embodiments, for example, tissues adjacent the PFO are brought at least partially together and energy is applied to the tissues to acutely close the PFO with fewer steps and/or fewer device components than just described. For example, application of suction to appose tissues is not required in all embodiments. Furthermore, a variety of different types of energy may be applied to the tissues from a variety of differently configured energy transmission devices. In some embodiments, one or more of the steps described above may be repeated one or more times, such as by repeating a tissue welding step. The above description, therefore, is provided for exemplary purposes only.

Although the foregoing description is complete and accurate, it has described only exemplary embodiments of the invention. Various changes, additions, deletions and the like may be made to one or more embodiments of the invention without departing from the scope of the invention. Additionally, different elements of the invention could be combined to achieve any of the effects described above. Thus, the description above is provided for exemplary purposes only and should not be interpreted to limit the scope of the invention as set forth in the following claims.

What is claimed is:

1. A method of treating a patent foramen ovale (PFO) having a right side and a left side in a heart of a patient, the method comprising:
   positioning a distal portion of an elongate catheter device proximate to tissues of a PFO, the catheter comprising a backstop apparatus deployable from the catheter body;
   delivering the backstop apparatus in the left atrium as to bring the PFO tissues at least partially together; and
   applying energy to the tissues with the catheter device to substantially close the PFO,
   wherein the energy is applied only from the right side of the heart.

2. The method of claim 1, wherein the backstop apparatus comprises a balloon.

3. The method of claim 1, wherein the backstop apparatus comprises a wire.

4. The method of claim 3, wherein the wire comprises a looped or coiled wire.

5. The method of claim 1, the backstop apparatus comprises an inferior bias as to selectively engage PFO tissues of the left atrium without substantially engaging a left atrial wall.

6. The method of claim 1, the backstop apparatus comprises at least a portion of an energy delivery system.

7. The method of claim 6, energy delivery system is a bipolar RF delivery system.

8. The method of claim 1, further comprising holding the tissues together after the energy has been applied.

9. The method of claim 1, wherein applying energy comprises applying at least one of radiofrequency energy, cryogenic energy, heat energy, ultrasound energy, microwave energy and laser energy.

10. The method of claim 1, wherein applying energy comprises denaturing collagen in the tissues.

11. The method of claim 1, wherein applying energy comprises renaturing collagen in the tissues.

12. The method of claim 3, further comprising keeping the tissues in apposition to allow collagen in the tissues to denature, reorganize and bind together to form a stable tissue bridge.

13. The method of claim 1, further comprising withdrawing the distal portion of the elongate catheter through the PFO tunnel following energy application.

14. The method of claim 1, wherein the distal portion of the catheter extends through the PFO tunnel.

* * * * *